(12) United States Patent
Perez et al.

(10) Patent No.: US 7,942,924 B1
(45) Date of Patent: May 17, 2011

(54) STAGED ENDOVASCULAR GRAFT DELIVERY SYSTEM

(75) Inventors: Juan I. Perez, Sunnyvale, CA (US); Matthew J. Fitz, Encinitas, CA (US); Robin W. Eckert, San Jose, CA (US); Octavian Iancea, Fremont, CA (US); Richard Newhauser, San Francisco, CA (US); David T. Pollock, San Mateo, CA (US); Timothy A. M. Chuter, Atherton, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 1165 days.

(21) Appl. No.: 10/091,172

(22) Filed: Mar. 4, 2002

(51) Int. Cl.
*A61F 2/00* (2006.01)
(52) U.S. Cl. .................................................. 623/1.23
(58) Field of Classification Search .............. 623/1.11, 623/1.13, 1.16, 1.2, 1.23, 1.15; 604/96.01; 606/108, 98
See application file for complete search history.

(56) References Cited

U.S. PATENT DOCUMENTS

| | | | |
|---|---|---|---|
| 5,562,724 A | 10/1996 | Vorwerk et al. | |
| 5,575,817 A | 11/1996 | Martin | |
| 5,639,278 A | 6/1997 | Dereume et al. | |
| 5,686,451 A | 11/1997 | Kristianson et al. | |
| 5,713,917 A | 2/1998 | Leonhardt et al. | |
| 5,833,694 A * | 11/1998 | Poncet | 623/1.11 |
| 5,957,974 A | 9/1999 | Thompson et al. | |
| 6,051,020 A | 4/2000 | Goicoechea et al. | |
| 6,090,136 A * | 7/2000 | McDonald et al. | 623/1.23 |
| 6,102,940 A | 8/2000 | Robichon et al. | |
| 6,120,522 A | 9/2000 | Vrba et al. | |
| 6,132,458 A * | 10/2000 | Staehle et al. | 623/1.11 |
| 6,162,246 A | 12/2000 | Barone | |
| 6,299,622 B1 * | 10/2001 | Snow et al. | 606/159 |
| 6,451,051 B2 * | 9/2002 | Drasler et al. | 623/1.15 |

FOREIGN PATENT DOCUMENTS
WO   WO 98/32399   7/1998

* cited by examiner

*Primary Examiner* — David Isabella
*Assistant Examiner* — Ann Schillinger
(74) *Attorney, Agent, or Firm* — Brooks, Cameron & Huebsch, PLLC

(57) ABSTRACT

The present invention embodies delivery systems and methods of packing an initial endovascular graft components for delivery that achieve a smaller delivery profile and reduce redundancy. Delivery systems and methods for packing the initial endovascular graft components for delivery facilitate a reduced delivery profile while allowing reliable positioning of the components before deployment.

25 Claims, 19 Drawing Sheets

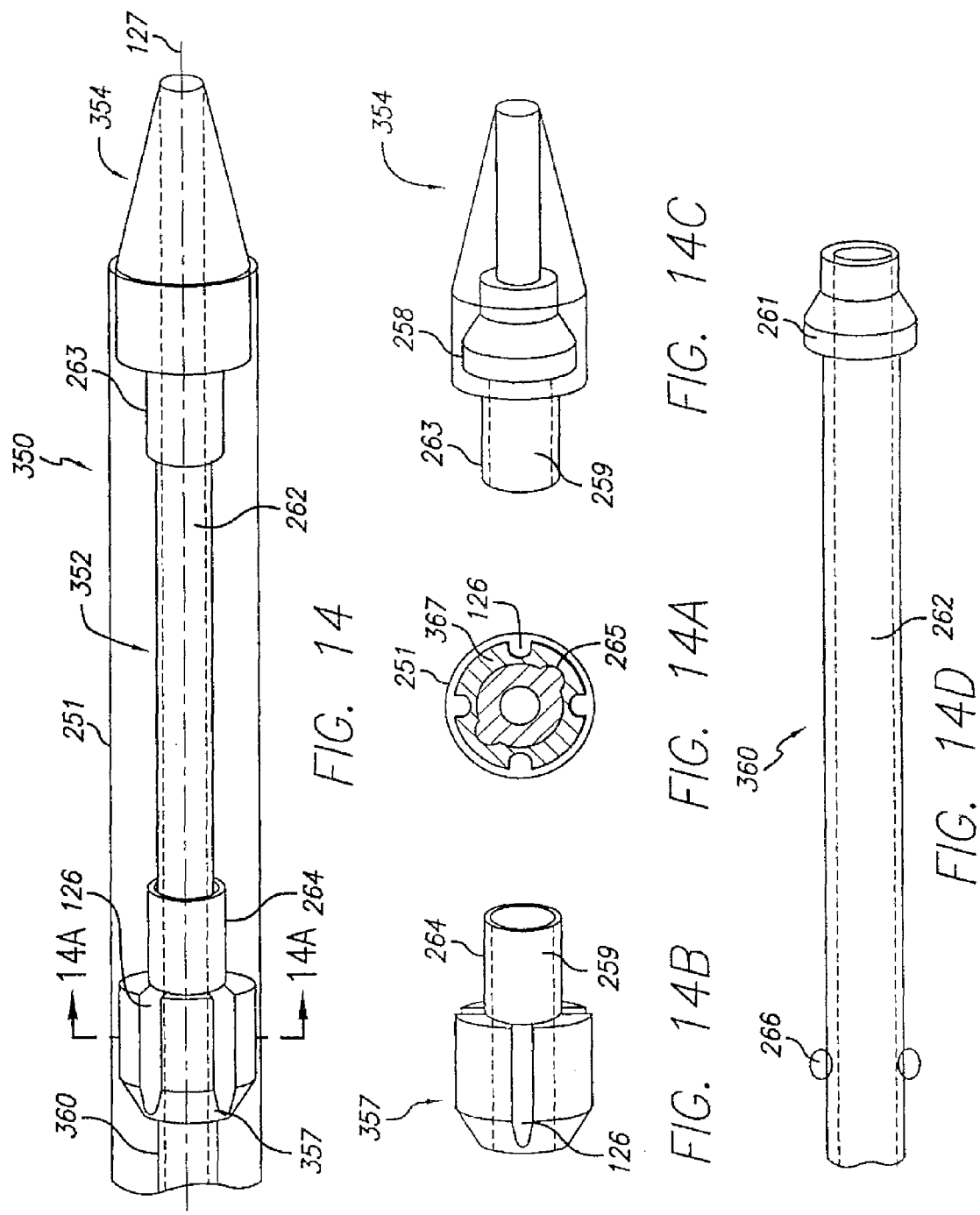

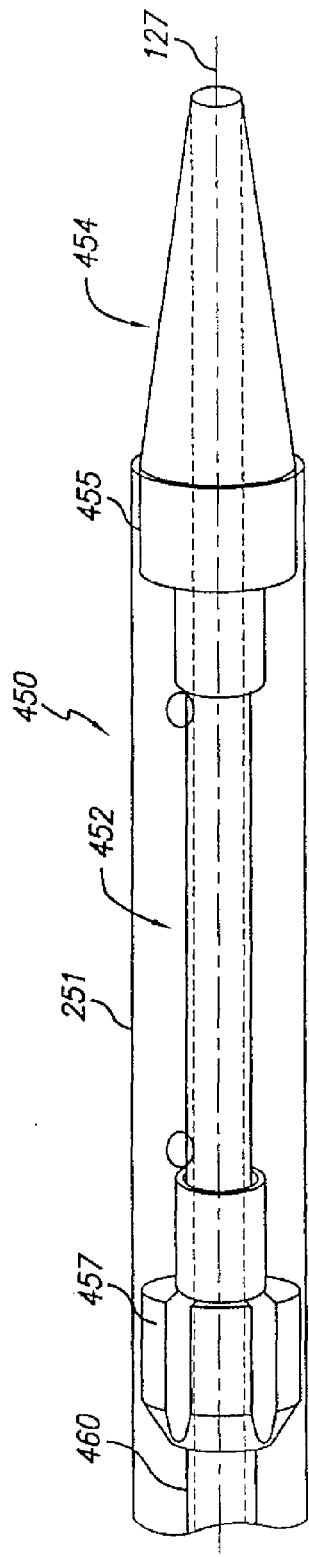
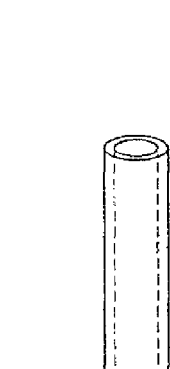
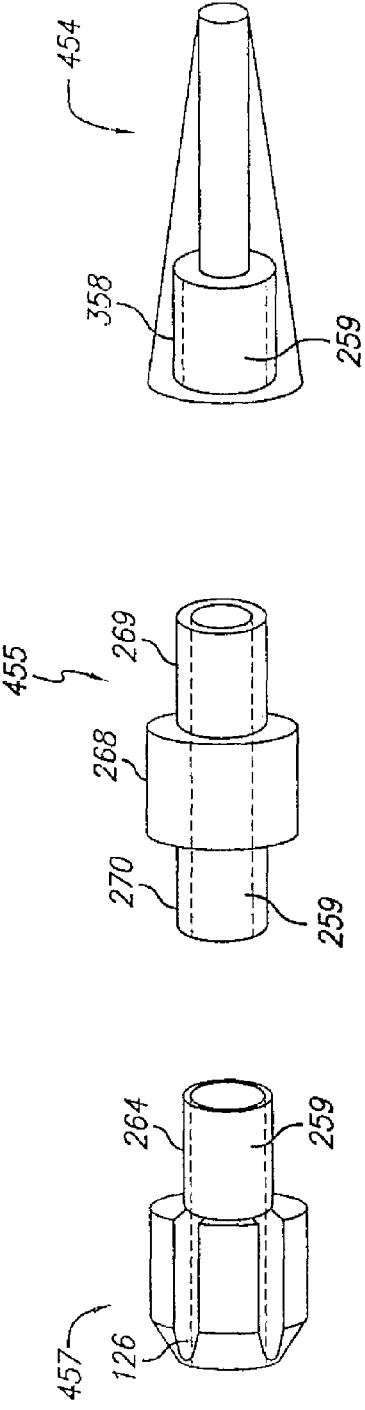
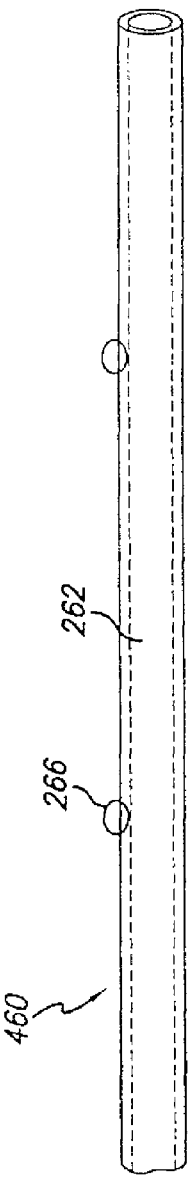

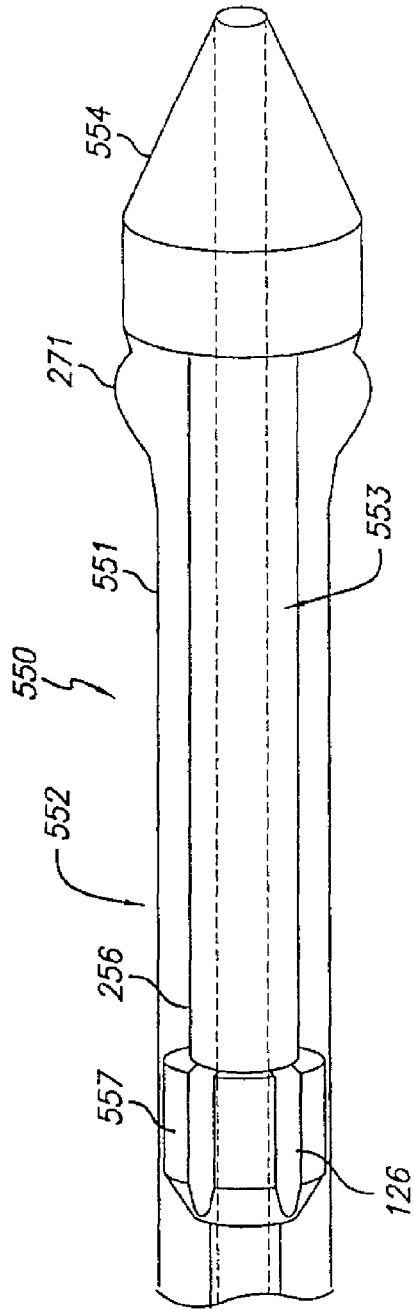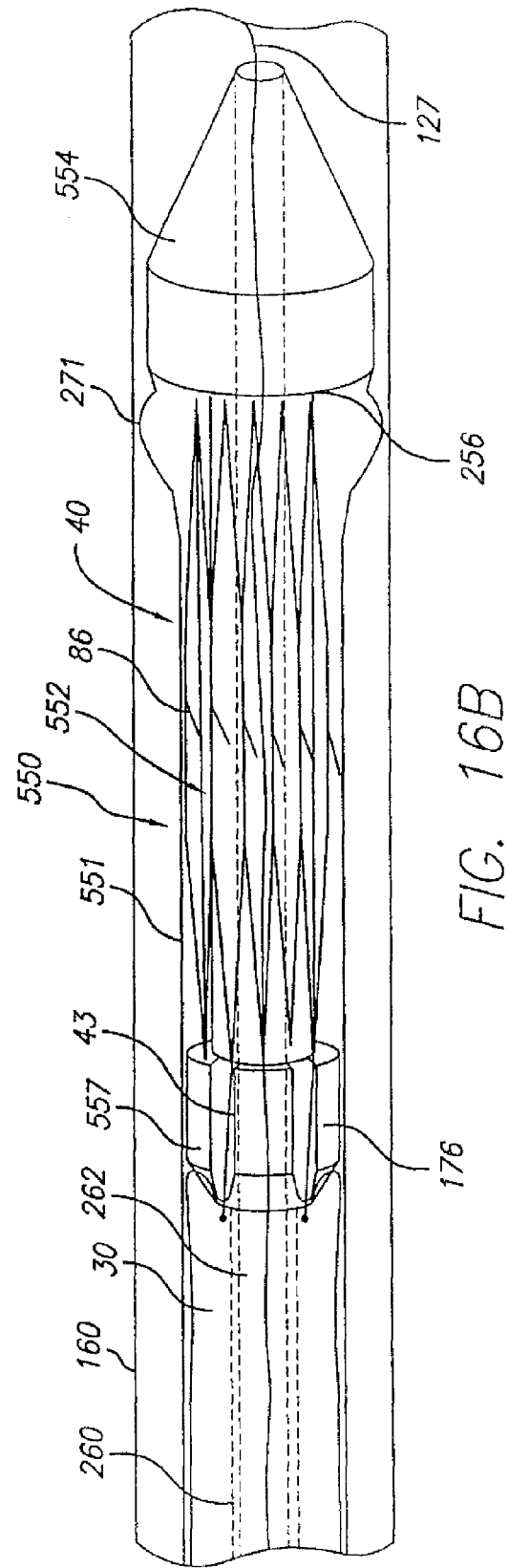
FIG. 16A
FIG. 16B

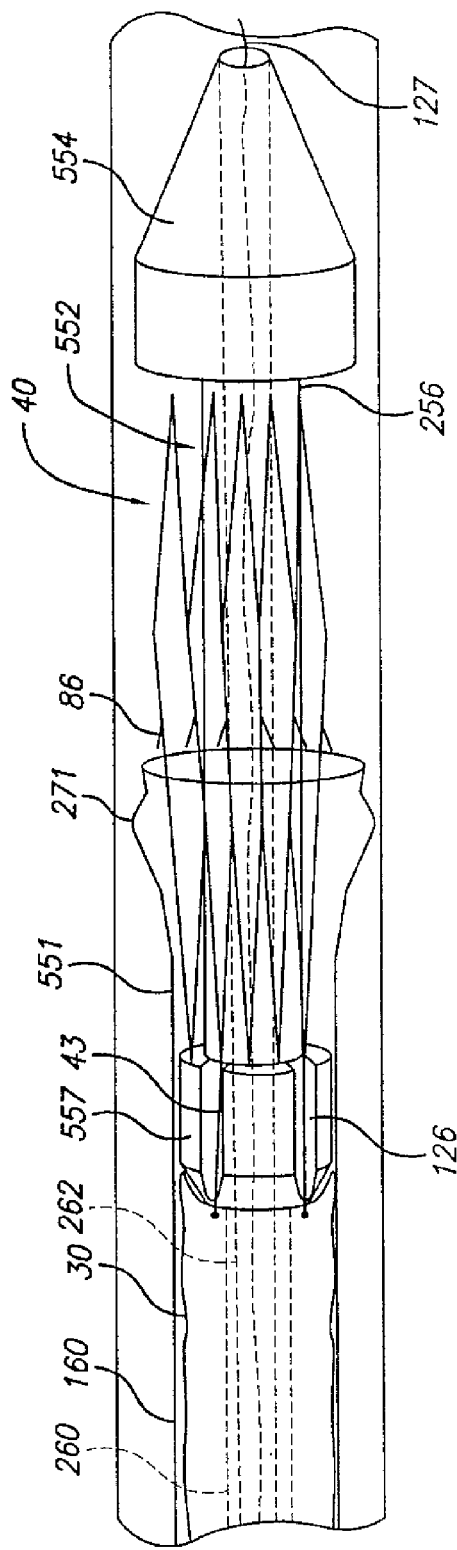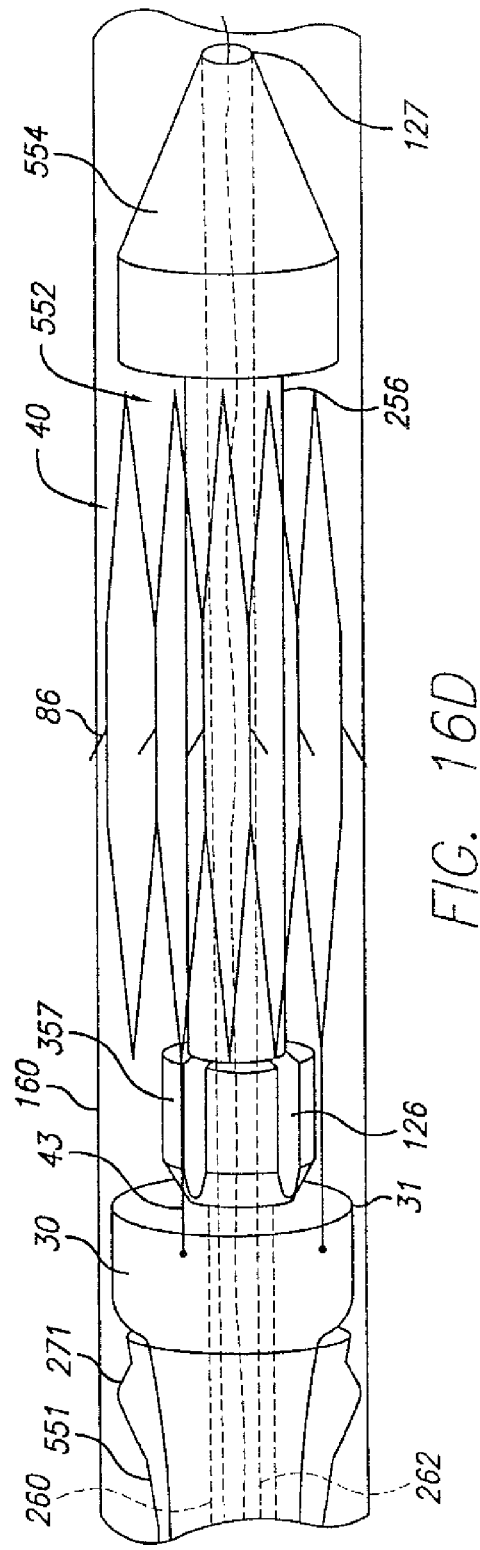

STAGED ENDOVASCULAR GRAFT DELIVERY SYSTEM

BACKGROUND OF THE INVENTION

This invention relates to methods for delivering and deploying modular sections of an endovascular stent/graft for assembly thereof within the vasculature of a patient and specifically to a system for accomplishing the same.

It is well established that various fluid conducting body or corporeal lumens, such as veins and arteries, may deteriorate or suffer trauma so that repair is necessary. For example, various types of aneurysms or other deteriorative diseases may effect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of matching individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods. Drawbacks with current methods can be categorized in three ways; drawbacks associated with delivery and deployment of the individual endovascular graft components, drawbacks associated with the main body portion, and drawbacks associated with securing the limb portions to the main body portion.

The drawbacks of current methods of delivery and deployment of endovascular graft components include redundant components for delivery, delivery of both a graft and its securing stent as a single entity, and at least minor surgery in order to gain access to the vasculature of the patient. Current methods for delivering the individual components of a modular endovascular graft to the treatment site require the use of a separate delivery catheter for each component and exchange of the delivery catheters through an introducer sheath after each component has been deployed. There are a number of disadvantages to this method. Since each delivery catheter has to be smaller than the introducer sheath, this limits the design of the implant, makes packing the implant into the delivery system more difficult, and increases the force required to deploy the implant. The use of multiple delivery catheters increases production costs and decreases reliability due to the multiplicity of catheter parts required. The process of removing one delivery system and replacing it with another may require coordination between two operators to ensure that guidewire access is maintained, a longer guidewire, additional procedure time, a large amount of physical space, and additional trauma to the insertion and delivery sites.

Furthermore, the known methods for delivering grafts to the required location within a patient's vascular system also require that an attachment system be delivered simultaneously with the graft, axially overlapping the graft and located either on the interior or the exterior of the graft's lumen, so that upon deployment of the graft the attachment system is expanded to attach the graft to the vascular wall. The attachment system is typically connected to the graft before implantation in the patient by means such as stitching. As a consequence, the outer diameter of the delivery capsule or sheath containing the compressed graft is increased by the presence of the compressed attachment system. Complications may be encountered in maneuvering the compressed graft and its delivery system around the bends and branches of the patient's vascular system. It will be appreciated that the greater the outer dimension of the capsule containing the compressed graft to be delivered, the more inflexible it will be, making delivery to the final destination more difficult and perhaps even impossible in some patients.

Moreover, in the majority of cases, the patient must be subject to surgery in which the appropriate vessel is surgically exposed and opened by incision to allow entry of the graft. Significantly, it is this surgical procedure on the vessel which gives rise to the most serious complications such as infection, patient discomfort, and necrosis of the vessel itself. However, if the outside dimension of the delivery capsule were sufficiently small, it might be possible, depending on the size and condition of the patient, to insert the capsule into the patient's vessel by applying sufficient force to the skin and artery of the patient with a sharpened end of the graft's delivery capsule, similar to the commonly known method of inserting a needle directly into the vein or artery of a patient.

The drawbacks of current embodiments of the main body component of a modular endovascular graft include a relatively large delivery profile due to the aforementioned graft and supporting stent as a single entity as well as additional stents within the separate branches of a bifurcated main body portion, difficulty in catheterizing the connection site of the first endovascular graft component prior to introduction of the second endovascular graft component, and a lack of adequate healthy tissue near the aneurysm for anchoring the graft to the aortic wall. Although the prior art has taught that the larger delivery profile of a combined graft and supporting stent can be minimized by providing separate support stents for the trunk and limb support branches of the main body component rather than a single support stent for the entire main graft component, separate support stents for the limb support branches are conventionally located at the same axial level. This results in a larger delivery profile since the support stents, when collapsed for delivery, lie on top of each other.

Furthermore, because of the restricted geometry of the vasculature and the small diameter of the limb supporting branch of the main body component, it can be difficult to insert one element of a modular endovascular graft into another. The instrumentation required to insert catheters and deploy the limb components of a modular endovascular graft inside the main graft limb support sections can dislodge mural thrombus in the AAA. The dislodged mural thrombus is carried in the blood flow through the femoral arteries to small distal arteries causing blockage and tissue necrosis.

Moreover, a lack of healthy tissue near the aneurysm being treated provides difficulty with adequately anchoring the main body portion of a modular endovascular graft. If the aneurysm is too close to the renal arteries there may be a lack of healthy tissue to adequately anchor the neck of the main graft portion without interfering with blood flow in the renal arteries. If the aneurysm extends too close to the bifurcation of the vasculature, there may be a lack of healthy tissue to adequately anchor the limb support branches of the main body component. Anchoring the limb support branches of the main body component in the iliac arteries requires a larger main body component and additional effort and delivery hardware. Allowing the limb support branches of the main body component to float freely in the aneurysm presents other difficulties with deploying the limb components of the modular endovascular graft within the main body component.

With regard to the method of delivery and deployment of endovascular graft components, there therefore exists a need for a endovascular graft delivery system that limits the amount of redundancy of delivery components required, can be easily operated by a single technician without decreased reliability or additional risk to the patient, facilitates a reduced outside dimension of the capsule or sheath containing a compressed graft component to be delivered to the patient's vascular system, and minimizes the need for surgery in order to gain entry to the patient's vasculature.

The devices and methods of the present invention addresses these and other needs.

SUMMARY OF THE INVENTION

Briefly and in general terms, the present invention is embodied in delivery systems and methods which minimize redundancy and profile and which are relatively easy to operate or perform.

An introducer sheath sufficiently long to reach the treatment site is provided. The introducer sheath acts to deliver an initial implant as well as a conduit to maneuver a plurality of subsequent implants into position and to restrain the implants until they are deployed into the body. The components of the system are deployed using the introducer sheath as the deployment catheter, obviating the need to have a second, larger sheath in place to exchange separate catheters.

A loading capsule which consists of a restraining sheath and a pusher assembly is also provided. The loading capsule is not a full catheter, but simply a short restraining sheath covering the implant. The loading capsule can be sized so that it is the approximately the same inner diameter as the introducer sheath. The loading capsule may have a fitting or lock that is designed to mate to a similar fitting on the introducer sheath. Once the loading capsule and introducer sheath have been mated together, a pusher assembly is used to transfer the collapsed implant from the loading capsule to the introducer sheath. The pusher is then used to push the implant down the length of the introducer into position. Once the physician is ready to deploy the implant, the pusher assembly is held in a fixed position and the introducer sheath is retracted, allowing the self-expanding implant to deploy.

The pusher assembly can be a tube similar to the inner lumen of a standard delivery system. Using one hand, the operator pushes the implant down the length of the introducer sheath. Following deployment, the operator removes the pusher assembly. Once the pusher assembly has been removed, more implant modules can be loaded and deployed using the same procedure.

Throughout this specification, the term "proximal" shall mean "nearest to the heart," and the term "distal" shall mean "furthest from the heart." Additionally, the term "ipsi-lateral" shall mean the limb of a bifurcated graft which is deployed using the same path through the vasculature that was used to deploy the main body component, and the term "contra-lateral" shall mean the limb of a bifurcated graft which is deployed using a second path through the vasculature which is catheterized after the main body component has been deployed. Furthermore, the term "inferior" shall mean "nearest the technician", and the term "superior" shall mean "farthest from the technician." Briefly and in general terms, the present invention is embodied in an endovascular graft composed of individual components delivered individually and assembled in-vivo and methods for delivering, deploying and assembling the same that eliminate the drawbacks described above.

In one aspect, the invention includes a delivery system and method for its use that facilitates delivery of the components of an endovascular graft with a reduced delivery profile over a tortuous route through vasculature, but requires little redundancy of delivery devices and can be operated by a single technician with minimal or no surgery required in order to gain entry to the patient's vasculature. Two embodiments of the delivery system and method are contemplated. Both embodiments are composed of devices that facilitate delivery and deployment of the main body and limb components described herein.

In a preferred embodiment, the delivery system has an introducer sheath assembly, loading capsule, self-expanding endovascular graft and a pusher assembly. The introducer sheath is sufficiently long to reach the treatment site. This introducer sheath tracks over a guidewire and maneuver the endovascular graft components into position and restrain the components in their constrained state until they are deployed. With the introducer sheath as the deployment catheter, the need for a second, larger sheath to exchange separate catheters is obviated. The loading capsule is a short, hollow restraining sheath covering the endovascular graft component and holding it in a constrained state. The loading capsule is mated with the introducer sheath and the pusher assembly is used to transfer the constrained endovascular graft component into the introducer sheath and to push the endovascular graft component to the intended position for deployment. The pusher assembly is placed over the guidewire after the loading capsule is mated to the introducer sheath. That is, the guidewire is configured to run through the introducer sheath and when the loading capsule is attached and locked to the introducer sheath, the guidewire is positioned to pass therethrough. A notch in the pusher assembly allows the guidewire to exit the pusher assembly without having to traverse its entire length. The operator can grasp the guidewire with one hand while using the other hand to push the constrained endovascular graft component into and through the introducer sheath. The self-expanding endovascular graft component is deployed by holding the pusher assembly in a fixed position while the introducer sheath is retracted. The pusher assembly is then removed by retracting it with one hand while holding the guidewire steady with the other hand. Multiple endovascular graft components can be delivered and deployed using the same procedure.

In an alternate embodiment, the delivery system has a single catheter which is used to deliver and deploy multiple self-expanding endovascular graft components. The catheter has an outer sleeve that can be retracted, thereby exposing an inner shaft that holds a self-expanding endovascular graft component. Each endovascular graft component deploys in succession as the catheter is maneuvered into position and the outer sleeve is retracted. The inner shaft is composed of a hypotube or lumen shaft with mechanical stops at the proximal and distal ends, component separators along the surface, and a rubber-like tip and inner endovascular graft support. The proximal end of the outer sleeve may be tapered with a outer ring of increased thickness and the outer surface of the proximal end of the inner shaft may contain grooves to facilitate retraction and capture of a partially-deployed stent prior to full deployment.

Other features and advantages of the present invention will become apparent from the following detailed description taken in conjunction with the accompanying drawings, which illustrate, by way of example, the principles of the invention.

BRIEF DESCRIPTION OF THE DRAWINGS

FIG. 14 is a partial perspective view, depicting an alternate embodiment of the delivery system shown in FIG. 13 having a separate molded flexible tip and distal stent stop attached to a hypotube/lumen;

FIG. 14A is a cross-sectional view of the delivery system depicted in FIG. 14 taken along line 14A-14A;

FIG. 14B is a perspective view, depicting the molded flexible inferior stent stop of the delivery system shown in FIG. 14;

FIG. 14C is a perspective view, depicting the molded flexible tip of the delivery system shown in FIG. 14;

FIG. 14D is a perspective view, depicting the hypotube/lumen of the delivery system shown in FIG. 14;

FIG. 15 is a partial perspective view, depicting an alternate embodiment of the delivery system shown in FIG. 13 having a separate molded cone shaped flexible tip, hard superior stent stop, and hard inferior stent stop attached to a hypotube/lumen;

FIG. 15A is a perspective view, depicting the hard inferior stent stop of the delivery system shown in FIG. 15;

FIG. 15B is a perspective view, depicting the hard superior stent stop of the delivery system shown in FIG. 15;

FIG. 15C is a perspective view, depicting the molded cone-shaped flexible tip of the delivery system shown in FIG. 15;

FIG. 15D is a perspective view, depicting the hypotube/lumen of the delivery system shown in FIG. 15;

FIG. 16A is a partial perspective view, depicting an alternate embodiment of the delivery system shown in FIG. 13 having a tapered outer jacket;

FIG. 16B is a partial perspective view, depicting the delivery system shown in FIG. 16A restraining a compressed endovascular graft and inserted into the vasculature of a patient over a guidewire;

FIG. 16C is a partial perspective view, depicting the delivery system shown in FIG. 16A inserted into the vasculature of a patient and its tapered outer jacket retracted to partially deploy the compressed stent; and FIG. 16D is a partial perspective view, depicting the delivery system shown in FIG. 16A inserted into the vasculature of a patient and its tapered outer jacket retracted to fully deploy the compressed stent.

DETAILED DESCRIPTION OF THE PREFERRED EMBODIMENTS

The present invention relates to systems and methods for accurately delivering and deploying the individual components of a endovascular graft at a treatment site within a patient's vasculature.

In one aspect, the invention is embodied in a system and method that accomplishes delivering a main graft component within vasculature using a delivery system embodying a jacket which is retracted to deliver the main graft component. The jacket is left within the vasculature and the remaining portions of the delivery system are withdrawn. The jacket is then employed as a sheath and jacket for the advancement and delivery into vasculature of subsequent medical devices. The jacket includes a hemostatic seal that prevents bleeding when exchanging capsules. Each of the subsequent devices is initially held in a capsule that mates with a proximal end of the jacket and is advanced within the jacket using a pusher device. At the time of deployment, the pusher can be held stationary and the sheath withdrawn to deploy the subsequent devices at a desired location within the vasculature.

Figure 1:
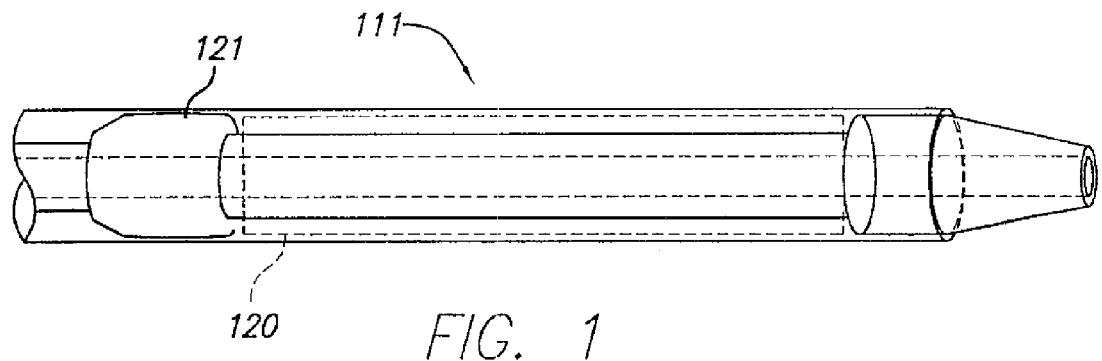
FIG. 1 is a perspective view, depicting an introducer sheath loaded with a medical device.
Figure 1A:
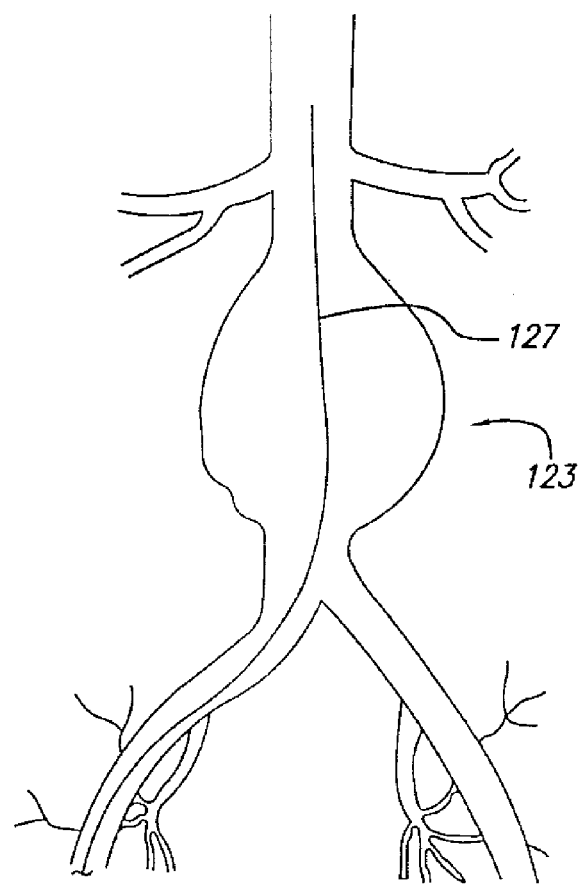
FIG. 1A is a partial cross-sectional view, depicting a first step in delivering a medical device within vasculature.
Figure 1D:
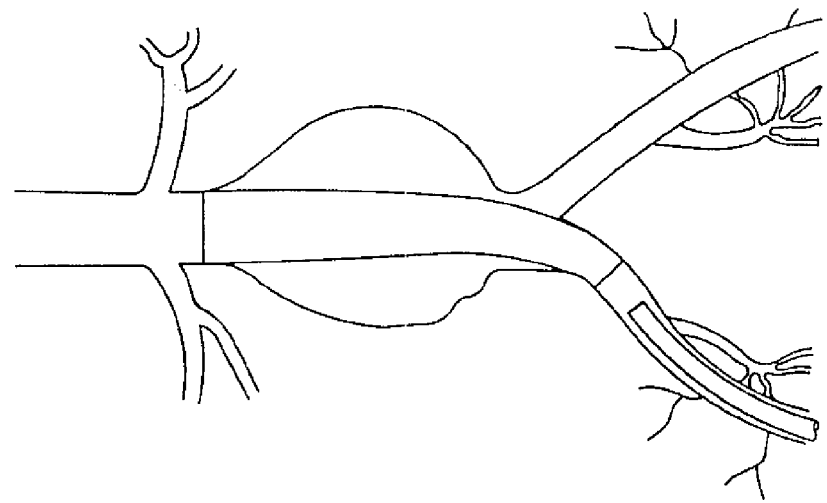
FIG. 1D is a partial cross-sectional view, depicting a fourth step in delivering a medical device within vasculature.
Figure 1C:
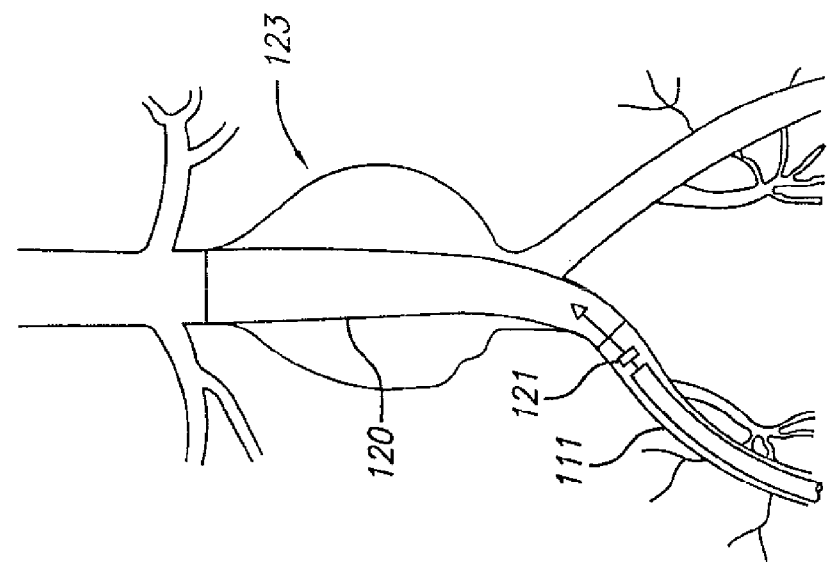
FIG. 1C is a partial cross-sectional view, depicting a third step in delivering a medical device within vasculature.
Figure 1B:
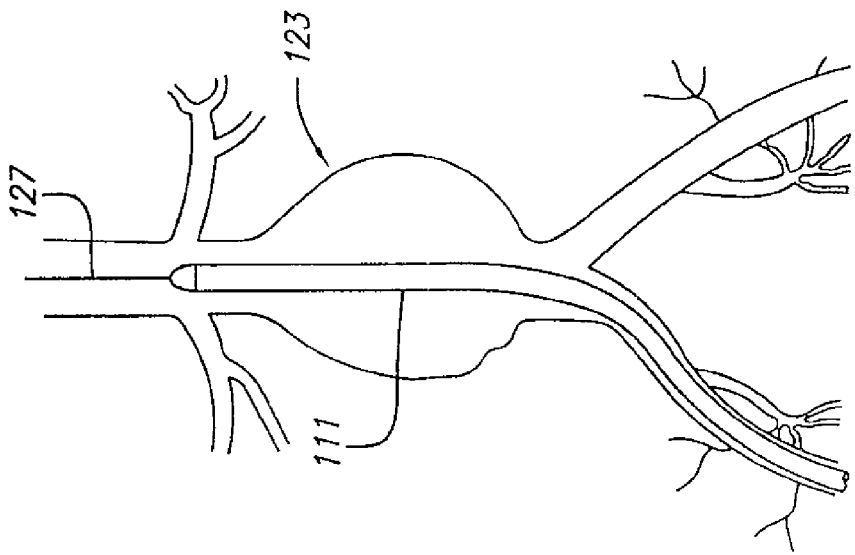
FIG. 1B is a partial cross-sectional view, depicting a second step in delivering a medical device within vasculature.
Figure 1E:
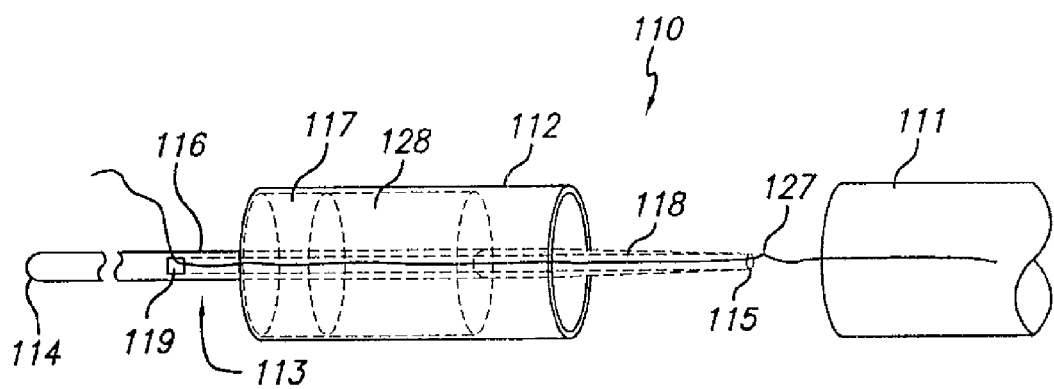
FIG. 1E is a perspective view, depicting a delivery system of the present invention having a loading capsule, pusher assembly, and introducer sheath.

FIGS. 1-1E shows a delivery system 110 that is one aspect of the present invention. The delivery system is defined by an introducer sheath 111 that is configured to receive a medical device such as an endovascular graft component 120 (shown in phantom in FIG. 1). The introducer sheath 111 is also configured to receive an initial pusher device 121 having a distal or inferior end (not shown) which extends exterior a patient's body when the introducer sheath assembly 111 is placed within vasculature.

In a first step involving the introducer 111 assembly, conventional techniques are employed to gain access to a patient's vasculature. A guidewire 127 is then placed within the vasculature and advanced beyond a repair site 123, which is shown in FIG. 1A as an aneurysm but can be any diseased or damaged blood vessel. The introducer sheath 111 loaded with a medical device 120 is advanced along the guidewire 127 to the repair site and while holding the initial pusher device 121 stable, the introducing sheath 111 is retracted thereby deploying the medical device 120 at the repair site 123. The pusher device 121 can then be withdrawn from the patient's vasculature leaving the introducer sheath 111 available for delivering additional medical devices within the patient's vasculature.

As shown in FIG. 1E, a loading capsule 112, and a rapid exchange pusher assembly 113 can be employed to deliver a subsequent compressed medical device or endovascular graft component 128 within vasculature. The introducer sheath 111, sufficiently long to reach the treatment site, acts as a conduit to maneuver the individual components of a endovascular graft 128 into position and restrain them in a compressed state until they are deployed in the body. The introducer sheath 111 acts as the delivery conduit, thereby obviating the need for a second sheath with a larger diameter to facilitate the exchange of individual catheters for each component delivered. The loading capsule 112 is a short restraining sheath that covers and retains the self-expanding endovascular graft 128 in a compressed state until it is transferred to the introducer sheath 111 for delivery to the treatment site 123. The inner diameter of the loading capsule 112 is approximately the same as the inner diameter of the introducer sheath 111 and may have a fitting or lock at its superior end that is designed to mate with a similar fitting or lock at the inferior end of the introducer sheath. The pusher assembly 113 is similar to the inner lumen of the standard delivery system and is defined by an inner tube 116 and a pusher button 117. The inner tube 116 is further defined by an inferior end 114, a tapered superior end 115, an exit notch 119, and a guidewire passageway 118 therethrough between the superior end 115 and exit notch 119. The guidewire passageway 118 facilitates placing the pusher assembly 113 over a guidewire 127 inserted in the introducer sheath. The rapid exchange exit notch 119 facilitates communication and control of the guidewire external to the pusher assembly 113 when the associated endovascular graft component 128 is delivered to and deployed at the treatment site. The endovascular graft component 128 is compressed for delivery about the pusher assembly tube 113 which extends past the superior end of the loading capsule 112. The pusher button 117 rests against or engages the compressed component in a manner to effect longitudinal advancement thereof and is covered by the loading capsule 112. There is a separate loading capsule and pusher assembly for each component delivered to the treatment site for deployment and assembly into the implanted endovascular graft 128.

Using this rapid exchange delivery system, a single operator can safely and efficiently deliver multiple self-expanding endovascular graft components within a patient's vasculature. The guidewire 127 is inserted in the guidewire passageway 118 at the superior end 115 of the pusher assembly 113 and threaded therethrough until it emerges from the rapid exchange exit notch 119. Once the guide wire 127 is threaded through passageway 118, the loading capsule 112 is attached to the introducer sheath 111. While holding the guidewire with one hand to prevent it from inadvertently moving, the operator pushes the inferior end of the pusher assembly with the other hand, thereby moving the compressed endovascular graft component and pusher button 117 through the loading capsule into the introducer sheath. By continuing to push the inferior end of the pusher assembly, the operator moves the compressed endovascular graft component to the superior end of the introducer sheath. With the pusher assembly held in a fixed position, the operator then retracts the introducer sheath, thereby allowing the compressed self-expanding endovascular graft component to deploy. The operator then retracts the pusher assembly with one hand, while holding the guidewire steady with the other hand in a rapid exchange manner. Successive compressed self-expanding endovascular graft components are delivered and deployed using this procedure.

In a preferred embodiment, the guidewire passageway 118 is a stainless steel hypotube with a wall thickness in the range of 0.003-0.010 inches or wall thickness-to-outer diameter ratio of 1:6 of which provides a strong, solid core which will not break or buckle under average conditions. The hypotube runs the entire length of the pusher assembly inner tube 116 and serves as a path for the guidewire 127 as well as providing increased rigidity for the delivery system 110 and a frame to which other components of the system may be attached. The hypotube may be a single segment or several segments of the same inner diameter or ever-increasing diameter. In the case of multiple segments, the hypo-tubes may be linked by welding, threading, gluing, or crimping. Alternately, multiple segments of hypotube may be linked by connecting threads or short tubes that overlap the segments and are crimped at both ends.

By providing an inner core of a single material as the guidewire passageway, obstruction of the guidewire due to multiple transitions of different materials and inner diameter is avoided. It is contemplated that a hypotube guidewire passageway may be utilized in any catheter system requiring the passage of a guidewire or other solid through a small diameter without obstruction.

Figure 2:
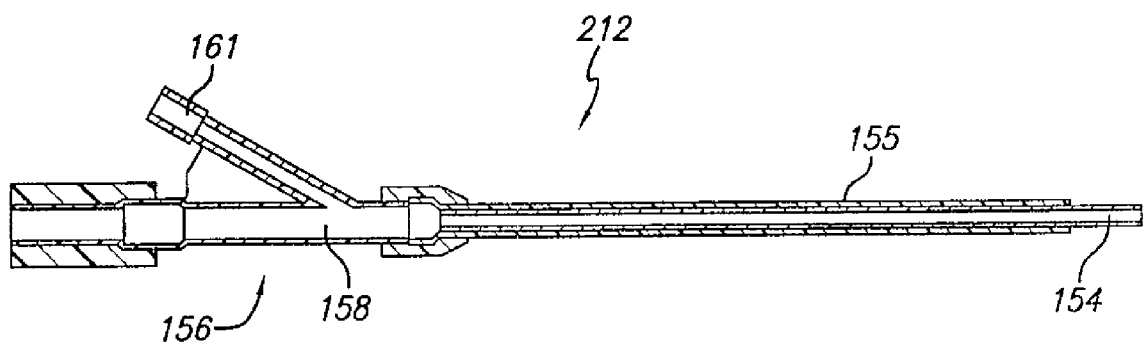
FIG. 2 is a cross-sectional view of an alternate embodiment of the loading capsule depicted in FIG. 1 having a soft plastic tube and short metal sleeve attached to a hard plastic body.

FIG. 2 depicts an alternate embodiment of the loading capsule shown in FIG. 1. The loading capsule 212 is defined by a short soft or hard plastic tube 154 such as polycarbonate, FEP, PTFE or HDPE surrounded by a shorter metal sleeve 155, the inferior ends of which are connected to a valve assembly 156. The valve assembly 156 is further defined by a through hole 158 and flushport 161. The tube 154 provides encapsulation for the compressed implant 128 such that it is isolated from the metal sleeve 155. The metal sleeve 155 provides a solid surface for engaging the inferior end of the introducer sheath 111 in order to transfer the compressed implant 128 and advance it to the implant site. The valve assembly 156 through hole 158 allows the pusher assembly 113, which protrudes from the inferior and superior ends of the loading capsule 212, to advance the compressed implant 128 from the tube 154 through the introducer sheath 111 to the implant site. The internal diameters of the tube 154 and metal sleeve 155 as well as the distance by which the tube 154 extends beyond the metal sleeve 155 in the superior direction are consistent with that of the introducer sheath, thereby allowing a smooth transition when the loading capsule 212 is mated to the introducer sheath.

One method of mating the loading capsule 212 to the introducer sheath 111 is shown in FIGS. 3A-E. The introducer sheath has a valve assembly 162 attached to the inferior end. The valve assembly is further defined by a knob 163 and back cap 164.

The knob 163 has a small diameter inferior portion 177, a wide diameter middle portion 165, flat extensions 166, external threads 167 near its superior end, a tapered nose 169, and a through hole 168. The inner diameter of the through hole 168 is slightly larger than the outer diameter of the loading capsule 212 metal sleeve 155. The tapered nose further embodies slots that define fingers 170. These fingers are bent inwards when sufficient pressure is applied. The flat extensions 166, which extend longitudinally from the wide diameter middle portion to the inferior end, facilitate turning the knob.

The back cap 164 is further defined by a flared inferior end 173, a through hole 174, threads 175 at the inferior end, an internal taper 176 toward the superior end, leading to a step-down diameter 178. The inner diameter and internal threads 175 of the through hole 174 accommodate the external threads 167 of the knob 163. The internal taper engages the tip of the knob, thereby causing the fingers to bend inward when the knob is screwed into the back cap. The step-down diameter is slightly larger than the outer diameter of the plastic tube 154 of the loading capsule 212.

Figure 3A:
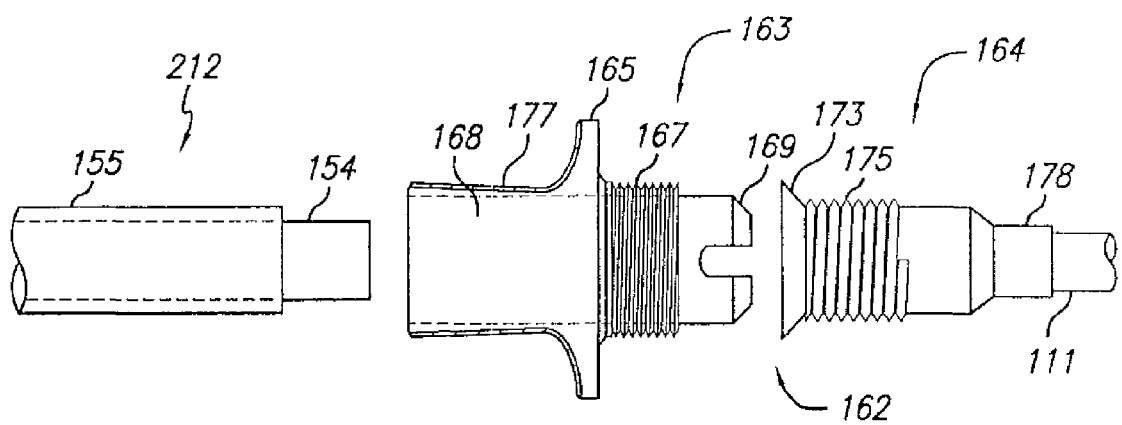
FIG. 3A is a partial perspective view of a loading capsule and an introducer sheath of the present invention having a valve assembly at the inferior end.
Figures 3B, 3C, 3D:
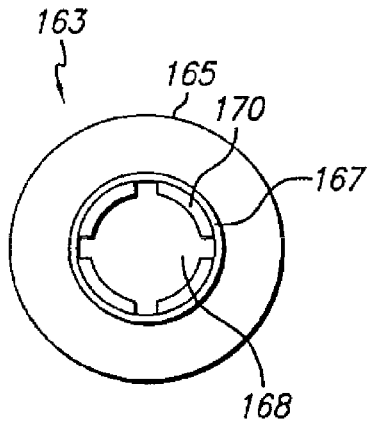
FIG. 3B is view of the introducer sheath valve assembly knob depicted in FIG. 3A from the inferior end.
FIG. 3C is view of the introducer sheath valve assembly knob depicted in FIG. 3A from the superior end.
FIG. 3D is view of the introducer sheath valve assembly back cap depicted in FIG. 3A from the superior end.
Figure 3E:
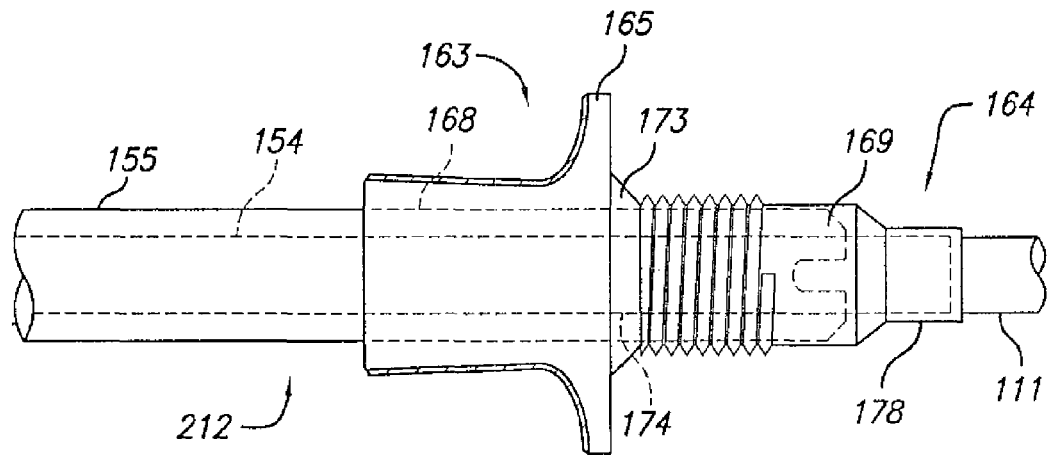
FIG. 3E is a partial perspective view of the joint formed when the capsule depicted in FIG. 2 is inserted in the valve assembly depicted in FIG. 3A with the knob tightened inside the back cap.

To mate the loading capsule 212 to the introducer sheath 111, the knob 163 is loosened from the back cap by unscrewing it in the inferior direction. The superior end of the loading capsule 212 is then inserted through the knob through hole 168 and inside the back cap 164 until the metal sleeve 155 reaches the step-down diameter 178. The step-down diameter 178 accommodates the tube 154, but prevents the metal sleeve 155 from advancing any further into the introducer sheath. Since the distance by which the tube 154 extends beyond the metal sleeve 155 in the superior direction is consistent with the length of the step-down diameter, the superior end of the tube 154 abuts the inferior end of the introducer sheath 111, thereby providing a smooth transition between the loading capsule and introducer sheath 111 inner diameters. When the knob 163 is tightened onto the back cap 164, the internal taper 176 of the back cap causes the fingers 170 of the knob to bend inward, thereby engaging the metal sleeve and locking it in place (FIG. 3E).

Once the metal sleeve is locked in place and the contents of the loading capsule are pushed through the introducer sheath to the implant site, the flat extensions of the knob facilitate torquing the introducer sheath as it is retracted. By torquing the introducer sheath, the operator may twist the implant as it is deployed, thereby facilitating correction of any twisting which occurred when the graft was compressed for delivery. The operator can use fluoroscopy to align the radio opaque markers 45 of the graft (FIG. 10) as it is deployed.

An alternate method of mating of the loading capsule 212 to the introducer sheath 111 is a small hard plastic "snap-fit" (not shown) attached to the superior end of the metal sleeve 155. The "snap-fit" has a key profile that matches a key profile on the inferior surface of the introducer sheath 111. The "snap-fit" prevents axial displacement of the loading capsule 212 and introducer sheath 111 as the compressed endovascular graft component 128 is transferred and the key profile prevents slippage under torque.

The hard plastic "snap-fit" may be attached to the metal sleeve by bonding with adhesive over a sand blasted surface. Alternately, the "snap-fit" may be attached by heat-staking to a knurled surface; heating the metal sleeve knurled surface so that when the hard plastic part is pressed against it, a thin layer of the plastic melts, thereby filling the grooves in the knurled surface and hardening over the metal sleeve as it is cooled.

Figure 4:
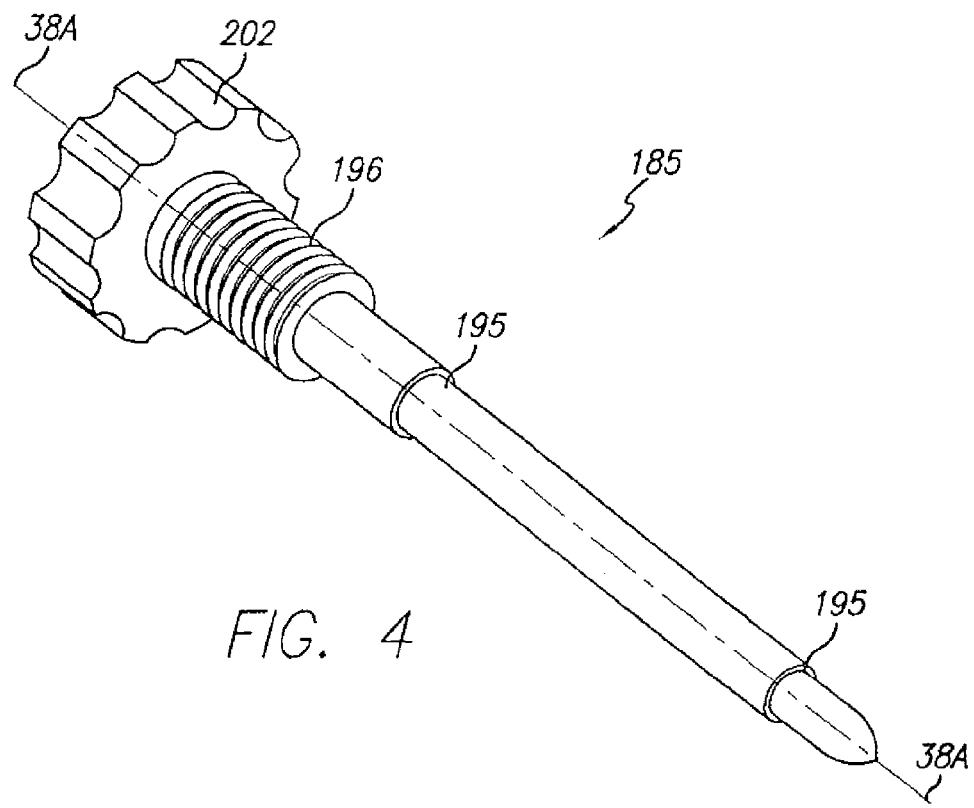
FIG. 4 is a perspective view depicting the fixture used to assemble a loading capsule of the present invention.
Figure 4A:
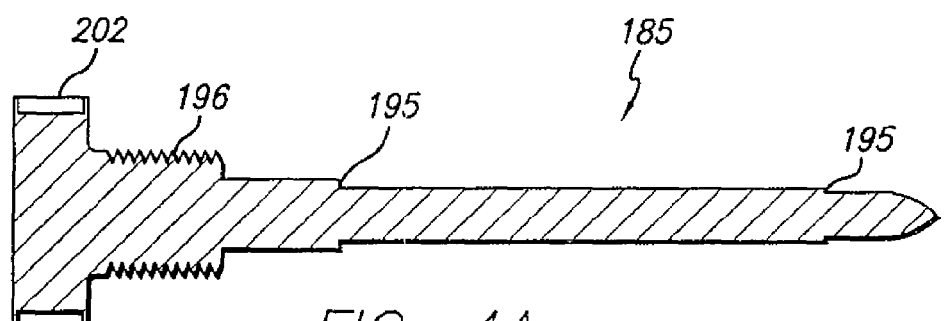
FIG. 4A is a cross-sectional view of the fixture depicted in FIG. 4 across the line 4A-4A.
Figure 4B:
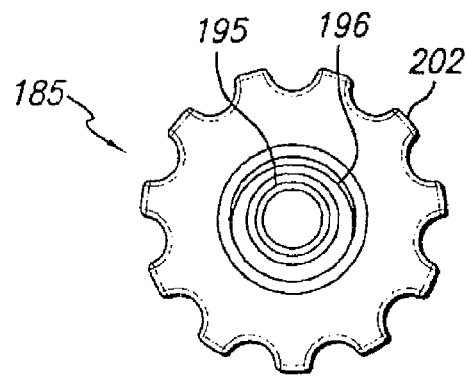
FIG. 4B is a view of the fixture depicted in FIG. 4 from the superior end.
Figure 4C:
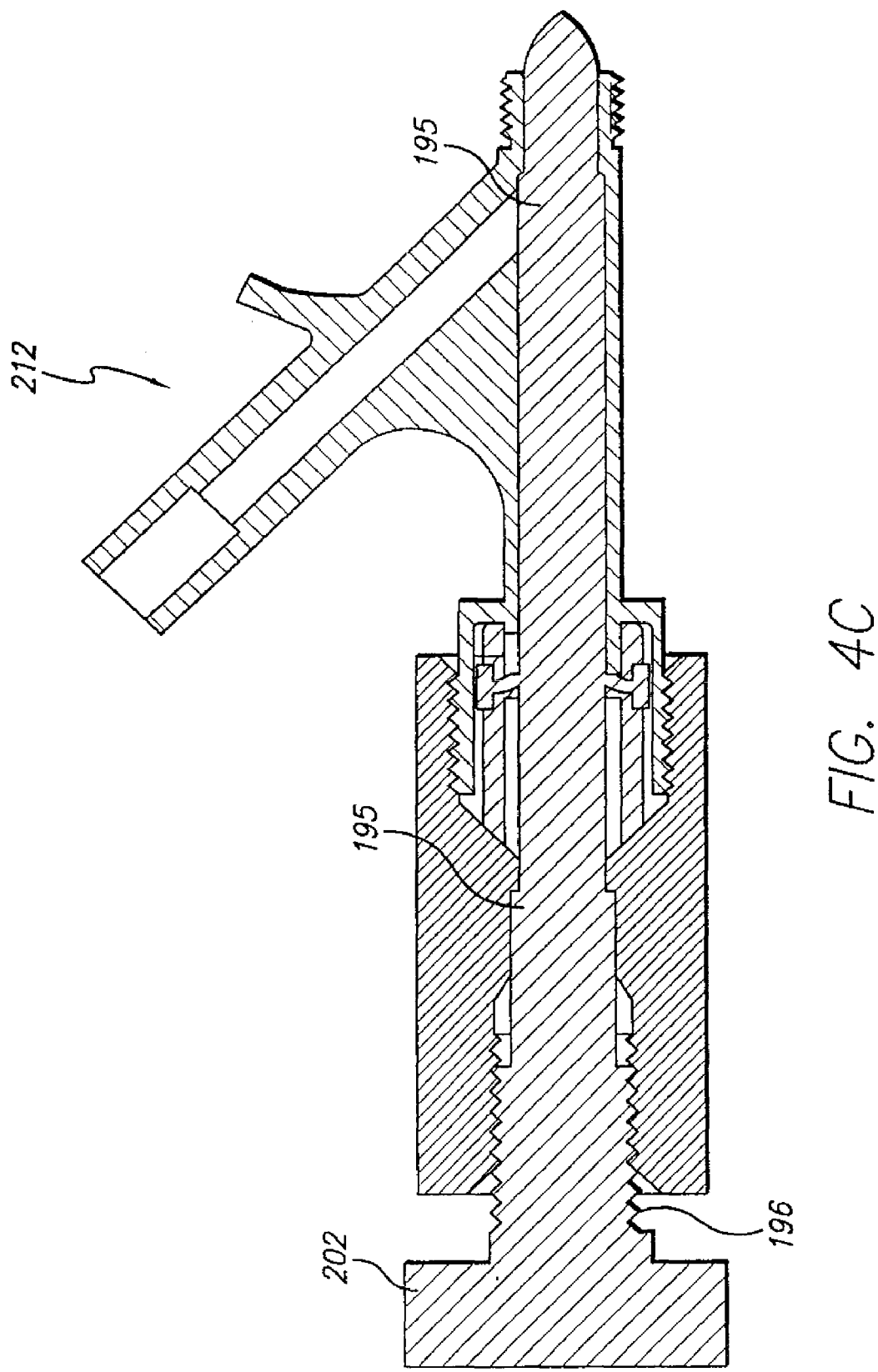
FIG. 4C is a cross-sectional view of a loading capsule of the present invention assembled using the fixture depicted in FIG. 4.

FIGS. 4-4C depict a staged and threaded steel fixture 185 to facilitate precise assembly of the introducer sheath distal end. The fixture 185 is defined by diametrical transitions 195 along its axis, threads 196 near the inferior end, and an inferior knob 202. The first component of the loading capsule assembly 212 is fixed in place by the threads 196 and inferiormost diametrical transition 195. The other components are screwed to the first component, the subsequent diametrical transitions 195 maintaining the proper axial spacing between them. The assembly of the components is as precise as the fixture 185, with minimum variation between the individual components, thereby producing an introducer sheath distal end which facilitates smooth docking and transfer of the compressed implant 128 from the loading capsule 212. It is contemplated such a fixture may be used whenever a device is assembled from components requiring stepped assemblies to precisely match each other with consistent internal distances between them.

Figure 5:
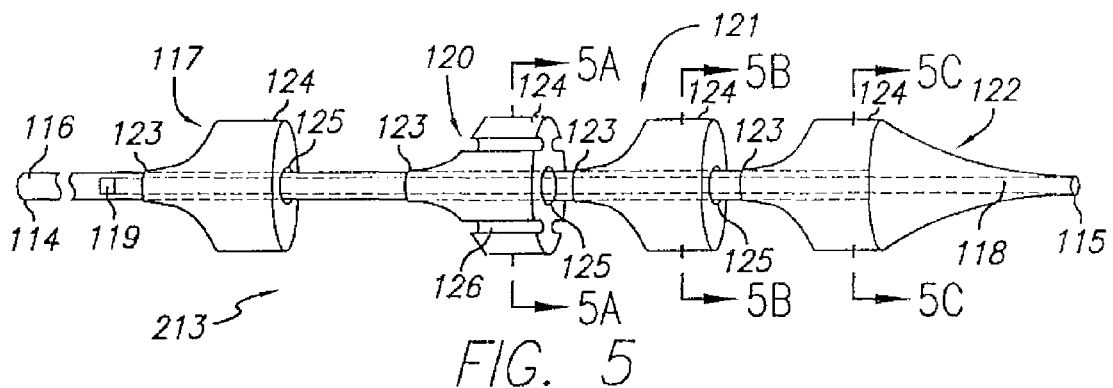
FIG. 5 is a perspective view of an alternate embodiment of the pusher assembly depicted in FIG. 1 with multiple pusher buttons.
Figure 5A:
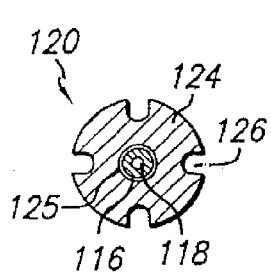
FIG. 5A is a cross-sectional view of the stent pusher button depicted in FIG. 5 taken at line 5A-5A.
Figure 5B:
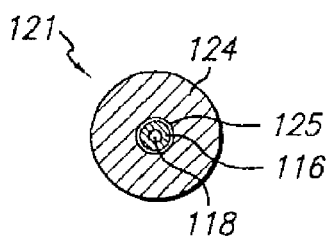
FIG. 5B is a cross-sectional view of the superior pusher button depicted in FIG. 5 taken at line 5B-5B.
Figure 5C:
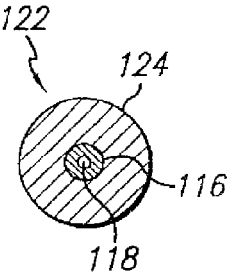
FIG. 5C is a cross-sectional view of the pusher assembly tip depicted in FIG. 5 taken at line 5C-5C.
Figure 5D:
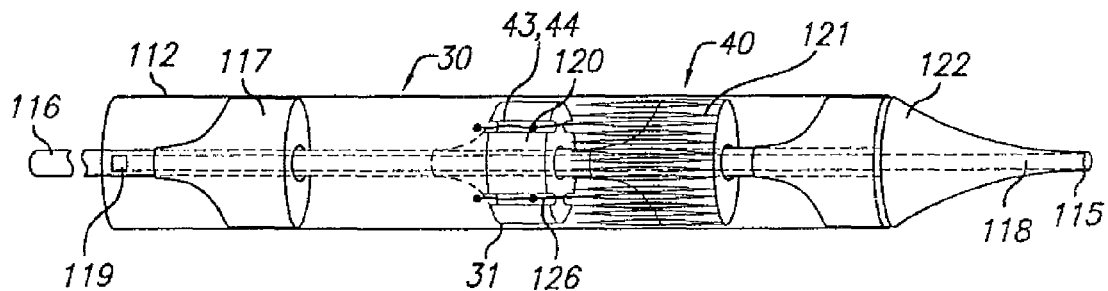
FIG. 5D is a perspective view of the pusher assembly depicted in FIG. 5 with a compressed attachment stent and graft held in place by a loading capsule.

FIGS. 5-5D depict an alternate embodiment of the pusher assembly shown in FIG. 1. The pusher assembly 213 is defined by a tapered flexible tip 122 and three pusher buttons mounted on the inner tube 116; an inferior graft pusher button 117, a stent pusher button 120, and a superior pusher button 121. The tapered flexible tip 122, which has a hollow center to allow the guidewire passageway 118 to pass therethrough, facilitates maneuvering the pusher assembly into and through the introducer sheath 111. It is contemplated that the flexible tip may be a stand-alone component (as shown) or may be attached to the superior end of the superior pusher button 121. The pusher buttons 117, 120, 121 facilitate packing the compressed endovascular graft 128 for delivery and control of the endovascular graft 128 when it is deployed. Each pusher button is an annular cylinder defined by a conical inferior portion 123, a cylindrical superior portion 124, and a through hole 125. The conical inferior portion facilitates retracting the delivery system into the sheath after the stent and graft have been deployed. The superior portion, which has an outer diameter approximately that of the compressed components, transmits force to the superior end of the delivery system when it is moved through the introducer sheath and minimizes the likelihood of the compressed components catching on the introducer sheath as the pusher assembly is maneuvered to the treatment site. Additionally, the conical inferior portion of the graft and stent pusher buttons further facilitate compressing the component around the pusher assembly tube. The through hole 125 allows the pusher assembly tube 116, and guidewire passageway therein, to pass through each pusher button. It is contemplated that the pusher buttons may be located at any axial position along the component and that additional pusher buttons may be provided to facilitate control of different portions of the same component.

The stent pusher button 120 may have axial grooves 126 along the external surface to facilitate packing the extended struts 43 or connector loops 44 of an attachment stent 40 (see FIG. 5D). Alternately, the axial grooves 126 may be used with a separately-deployed attachment or support stent having enlarged inferior stent ends in order to facilitate control of the stent prior and during deployment.

Figure 6A:
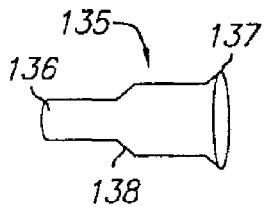
FIG. 6A is an enlarged perspective view of a crimp sleeve of the present invention.
Figure 6B:
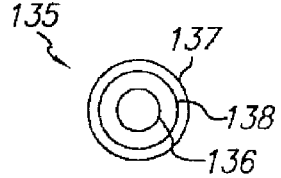
FIG. 6B is view of the crimp sleeve depicted in FIG. 6A from the inferior end.
Figure 6C:
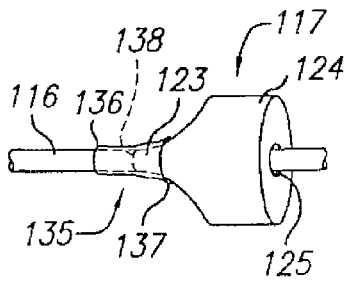
FIG. 6C is a perspective view of a crimp sleeve installed over the crimp area formed between a pusher button and pusher assembly tube of a the present invention.

The pusher buttons 117, 120, 121 and flexible tip 122 may be attached to the pusher assembly tube 116 by crimping the inferior portion 123 to the pusher assembly tube and covering the crimp area with a custom funnel-like crimp sleeve 135 as shown in FIGS. 6-6C. The crimp sleeve 135 is defined by an inferior end 136 having an outer diameter that matches the outer diameter of the pusher assembly inner tube 116, a tapered middle portion 138, and a superior end 137 having an inner diameter not exceeding the diameter of the widest portion of the pusher button or flexible tip. The crimp sleeve 135 may be made of either steel or similar characteristic material depending on the application and sterilization method. By covering the crimped area with the crimp sleeve 135, the transition between the pusher assembly inner tube 116 and pusher button is completed without raised edges that can generate interference when the pusher assembly 213 is retracted into the introducer sheath 111 after the implant is deployed. It is contemplated that a crimp sleeve 135 may be used in any catheter system that requires consistent and smooth transitions between changing diameters along its length.

To apply the crimp sleeve 135, the narrow diameter inferior end 136 is slid over the pusher assembly tube 116. Next, the pusher button 117, 120, 121 or flexible tip 122 is attached to the pusher assembly inner tube 116 by crimping the inferior portion 123 to the tube. Finally, the crimp sleeve 135 is slid forward with its tapered portion 138 covering the crimp area and its superior end 137 bonded next to the superior portion 124 of the pusher button or flexible tip. In a preferred embodiment, the crimp sleeves 135 are made of stainless steel and bonded in place using a biocompatible adhesive such as Loctite 380.

Figure 8:
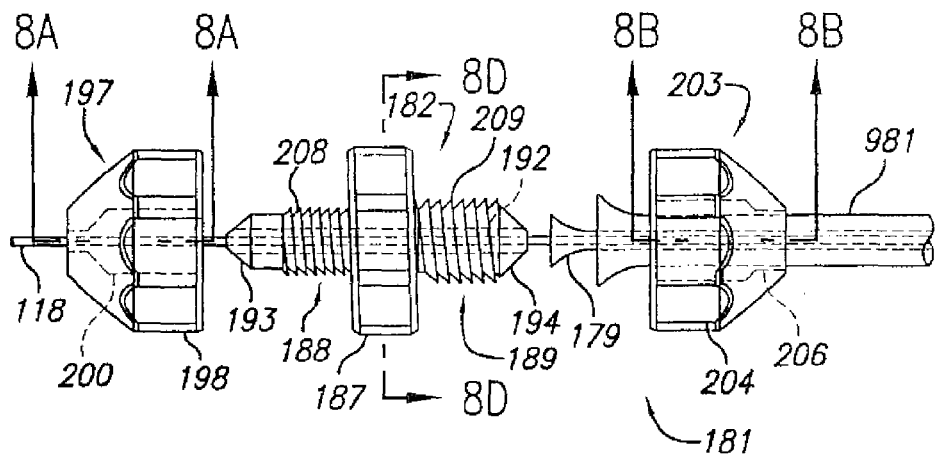
FIG. 8 is a perspective view of a locking system of the present invention with the two cap nuts disassembled from the center body with a Pebax tube, pusher assembly inner tube, and guidewire passageway inserted therein.
Figure 8A:
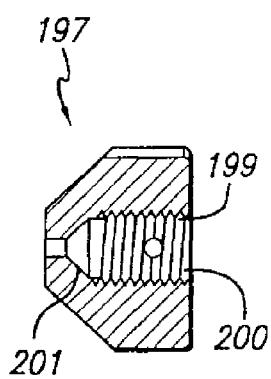
FIG. 8A is a cross-sectional view of the small diameter cap nut depicted in FIG. 8 taken at line 8A-8A.
Figure 8B:
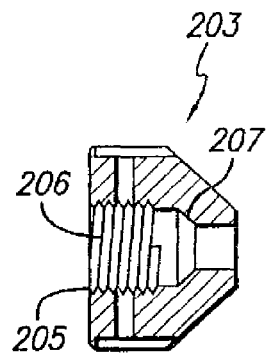
FIG. 8B is a cross-sectional view of the large diameter cap nut depicted in FIG. 8 taken at line 8B-8B.
Figure 8C:
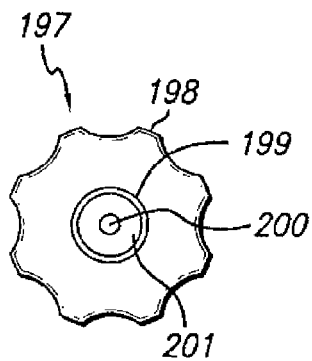
FIG. 8C is a view of the small diameter cap nut depicted in FIG. 8 from the superior side.
Figure 8D:
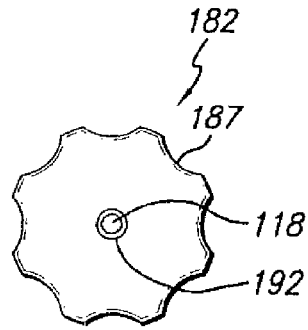
FIG. 8D is a cross-sectional view of the center body depicted in FIG. 8 taken at line 8D-8D.

In a preferred embodiment the pusher assembly 213 at its distal end is a Pebax shaft 179 with a stainless steel tube 901 (FIG. 8). The outer diameter of the Pebax shaft 179 is reduced at the inferior end to fit inside the stainless steel tube 901 such that the outer diameter of the pusher assembly 213 remains consistent throughout its length. The stainless steel tube 901 at the inferior end increases the rigidity of the pusher assembly 213, thereby facilitating a more controlled and precise deployment of the implant. It is contemplated to use a stainless steel tube 901 to reinforce the pusher assembly 213 whenever retraction forces are increased by the size of the implant or tortuosity of the anatomy. It is also contemplated that a stainless steel tube 901 may be used to reinforce a pusher assembly in catheter based delivery systems with an outer diameter of 8 Fr to 18 Fr. Also in the preferred embodiment, the gap between the Pebax shaft 179 and introducer sheath 111 is 0.006"+0.002".

Figure 7:
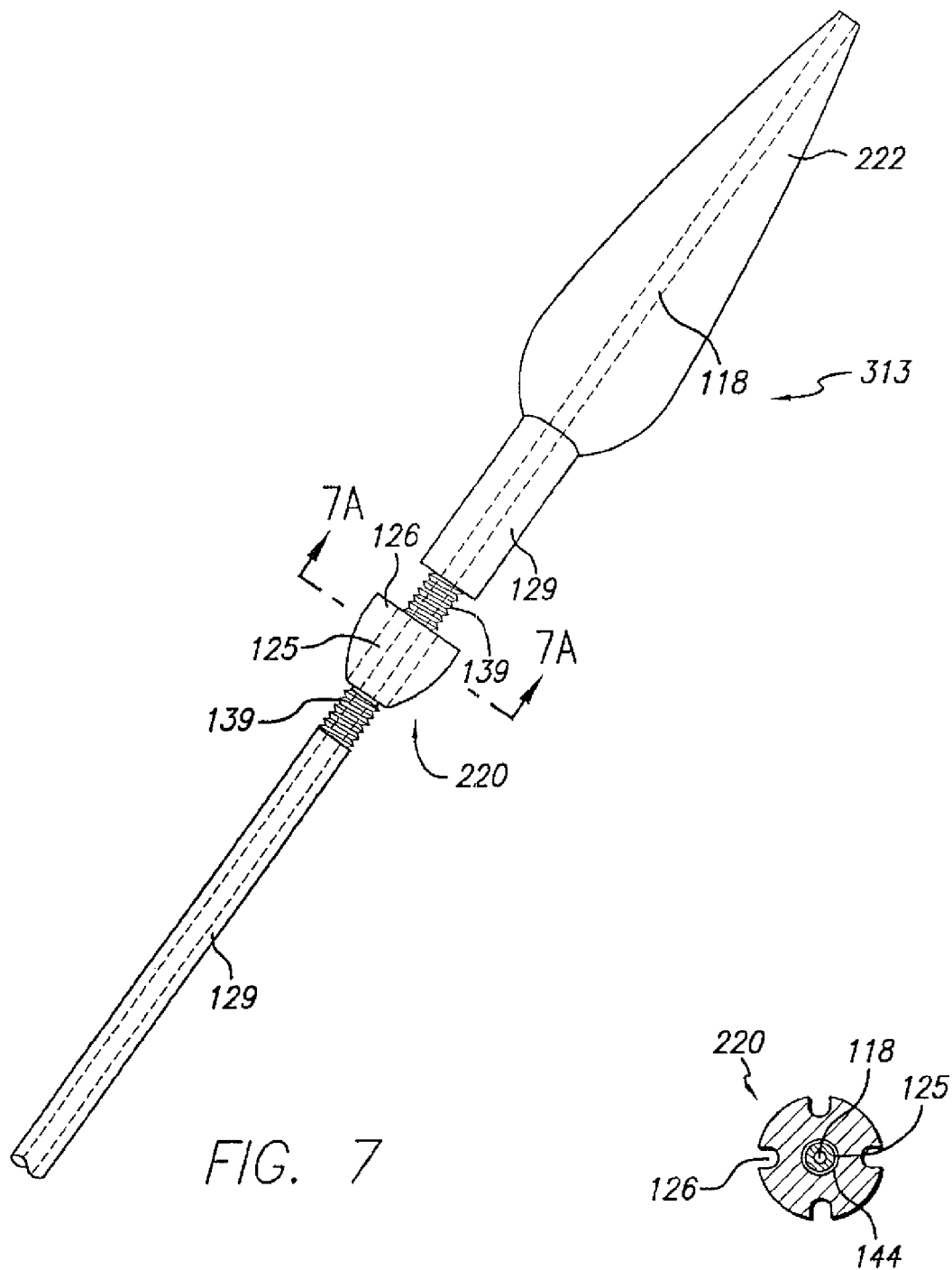
FIG. 7 is a perspective view of an alternate embodiment of the pusher assembly depicted in FIG. 1 with the components joined via threaded hypotube sections.
Figure 7A:
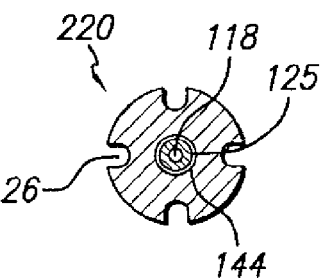
FIG. 7A is a cross-sectional view of the pusher button depicted in FIG. 7 taken at line 7A-7A.
Figure 7B:
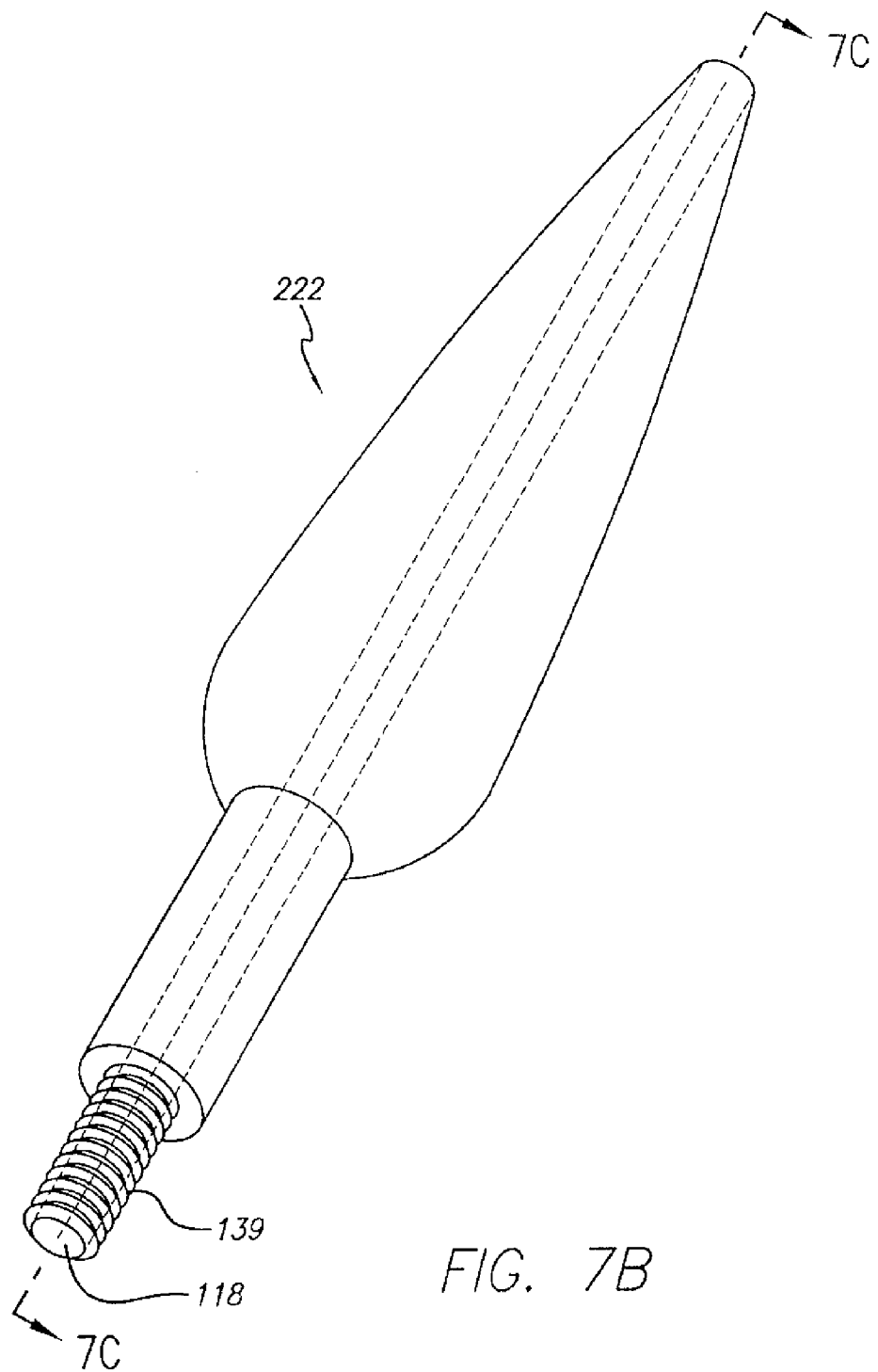
FIG. 7B is a perspective view of the flexible tip of the pusher assembly depicted in FIG. 7.
Figure 7C:
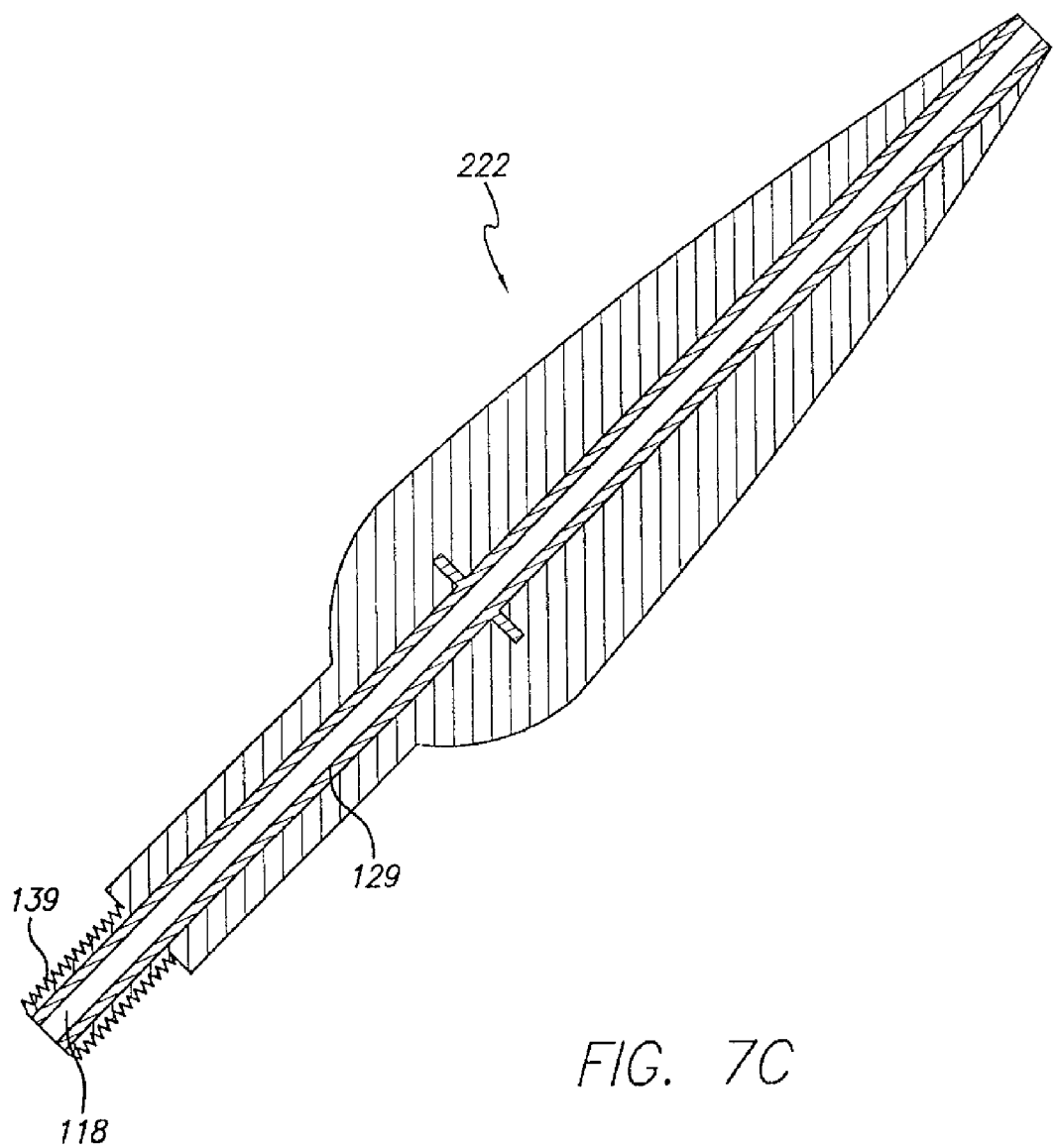
FIG. 7C is a cross-sectional view of the flexible depicted in FIG. 7B taken at line 7C-7C.

FIGS. 7-7C depict another alternate embodiment of the pusher assembly shown in FIG. 1 which utilizes threads to attach the components of the pusher assembly. The pusher assembly 313 is defined by a tapered flexible tip 222, a pusher button 220, and sections of threaded hypotube 129. The tapered flexible tip is over molded on a core hypotube section 129 having a guidewire passageway 118 therethrough and external threads 139 at the inferior end. The pusher button 220 is defined by external axial grooves 126 and a through hole 125 with internal threads 144 which mate with the hypotube 129 external threads 139. The pusher assembly 313 is formed by attaching the superior end of the pusher button 220 to the threaded inferior end of the flexible tip 222 core hypotube 129 and attaching another hypotube section 129 with threads 139 at its superior end to the inferior end of the pusher button 220.

It is contemplated that additional pusher buttons 220 with internal threads may be added to the pusher assembly 313 by utilizing hypotube sections 129 having external threads 139 at both the superior and inferior ends. In a preferred embodiment, each hypotube section 129 has approximately five threads 139 of size #0-80 UNF, each pusher button 220 has matching internal threads, and the flexible tip 222 is formed by plastic injection molding over a core hypotube section 129 with a mechanical feature such as a crimp to prevent rotation or slippage.

Figure 8E:
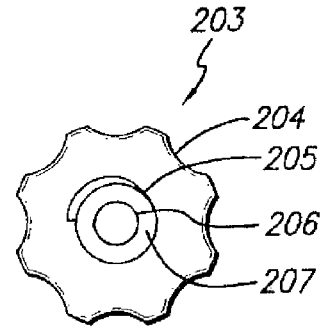
FIG. 8E is a view of the large diameter cap nut depicted in FIG. 8 from the inferior side.

Since the pusher assembly inner tube 116 must be long enough to allow the graft to be pushed through the introducer sheath 111 to the implant site, such as to the abdominal aorta, the tube 116 may extend a considerable distance in the inferior direction from the inferior pusher button 117 (FIG. 5). A hollow Pebax tube 179 may enclose the pusher assembly inner tube 116 from the inferior end 114 of the pusher assembly to the inferior pusher button 117 in order to maintain a consistent diameter for the delivery system 110 (FIG. 1E). FIGS. 8-8E show a method of securing the pusher assembly inner tube 116 to the hollow Pebax tube 179 and stainless steel tube 901 at the inferior end 114 of the delivery system 110. The locking system 181 is defined by a disc shaped center body 182, an inferior cap nut 197, and an superior cap nut 203. The center body 182 is further defined by a grip 187 around its center edge, an inferior protruding cylinder 188 with external threads 208, a superior protruding cylinder 189 with external threads 209, and a through hole 192. The inferior cylinder 188 has a slotted nose 193 which defines a series of fingers. The superior cylinder 189 has a tapered end 194. The inferior 197 and superior 203 cap nuts are further defined, respectively, by grips 198, 204, internal threads 199, 205, tapered internal ends 201, 207, and through holes 200, 206 at their axis.

Note that the superior cap nut 203 through hole 206 have a larger diameter than the inferior cap nut 198 through hole 200. The wide diameter superior cylinder 189 and superior cap nut 203 through hole 206 facilitate securing the hollow Pebax tube 179 and steel tube 901 to the center body 182. The wide diameter cap nut 203 through hole 206 facilitates passing the Pebax tube 179, pusher assembly inner tube 116, and steel tube 901 therethrough. The pusher assembly inner tube 116 passes through the center body 182, emerging from the slotted end 193 of the inferior cylinderl 88. The Pebax tube 179 and pusher assembly steel tube 901 have flared inferior ends which are sandwiched between the internal taper 207 of the superior cap nut 203 and tapered end 194 of the superior cylinder 189 when the superior cap nut 203 is tightened onto the superior protruding cylinder 189, thereby securing them to the center body 182 when the superior cap nut 203 is tightened.

The small diameter inferior cylinder 188 and inferior cap nut 197 facilitate securing the pusher assembly inner tube 116 to the center body 182. The inferior cap nut 197 through hole 200 facilitates passing the pusher assembly inner tube 116 therethrough. When the inferior cap nut 197 is tightened over the slotted nose 193 of the inferior cylinder 188, the fingers are compressed downward by the internal taper 201 of the inferior cap nut 197, thereby gripping the pusher assembly inner tube 116 and locking it in place. This way the pusher assembly inner tube 116, the Pebax tube 179 and pusher assembly steel tube 901 are mechanically secured to the center body 182.

Figure 9:
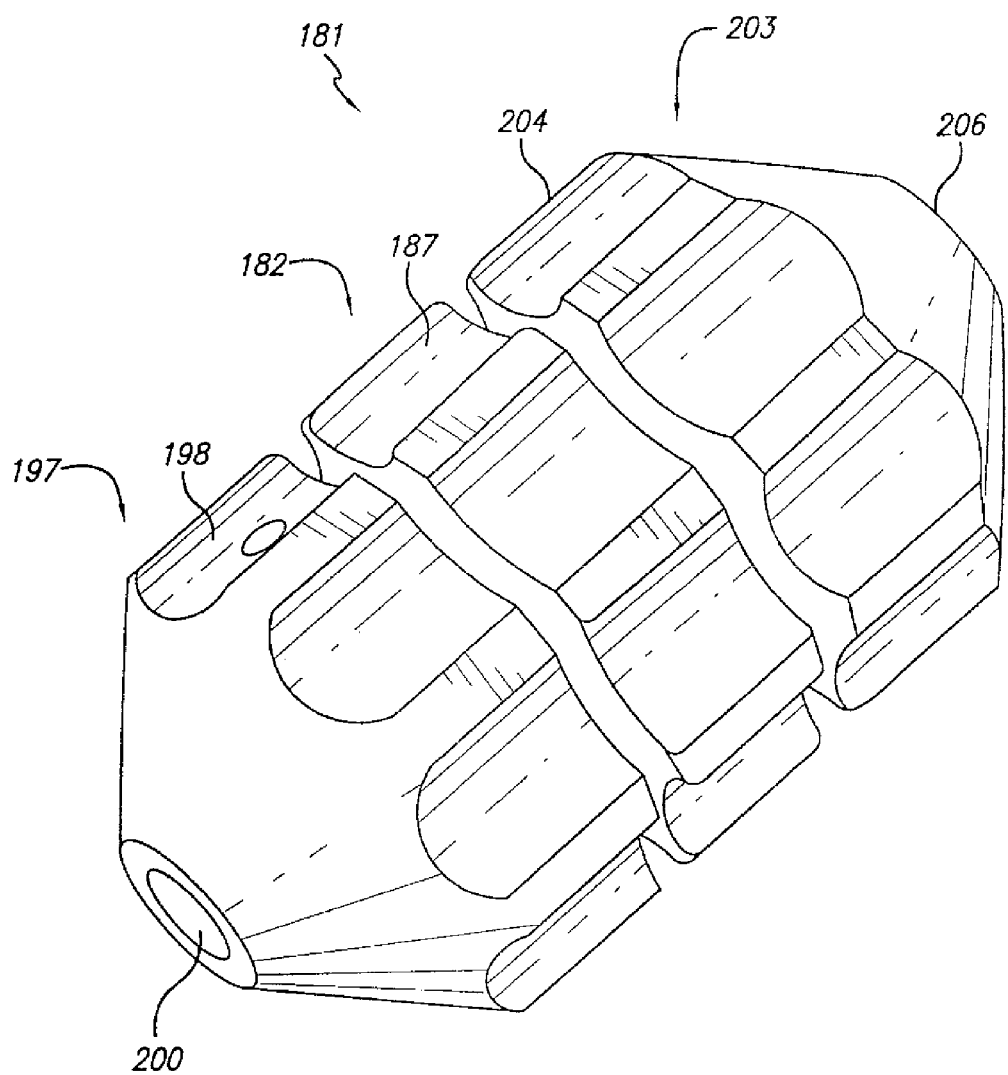
FIG. 9 is an enlarged perspective view of a locking system of the present invention with the two cap nuts installed on the center body.

The locking system 181 facilitates using a single pusher assembly inner tube 116 tube length for all components delivered to the treatment site instead of a different length for each component. By sliding the pusher assembly inner tube 116 forwards or backwards through the locking system 181, the desired exposure length at the packing location is achieved. Furthermore, the locking system 181 eliminates the need to use epoxy-bond to attach the pusher assembly inner tube 116 to the Pebax tube 179 and reduces the amount of crimps required during assembly. Moreover, as shown in FIG. 9, the center body 182 and cap nuts 197, 203 form a cylindrical handle grip for the pusher assembly 213 which provides an improved grip from a flat handle. It is contemplated that the locking system 181 may be used in any catheter-based delivery system intended to transport a range of implant components of varying lengths.

Figure 10:
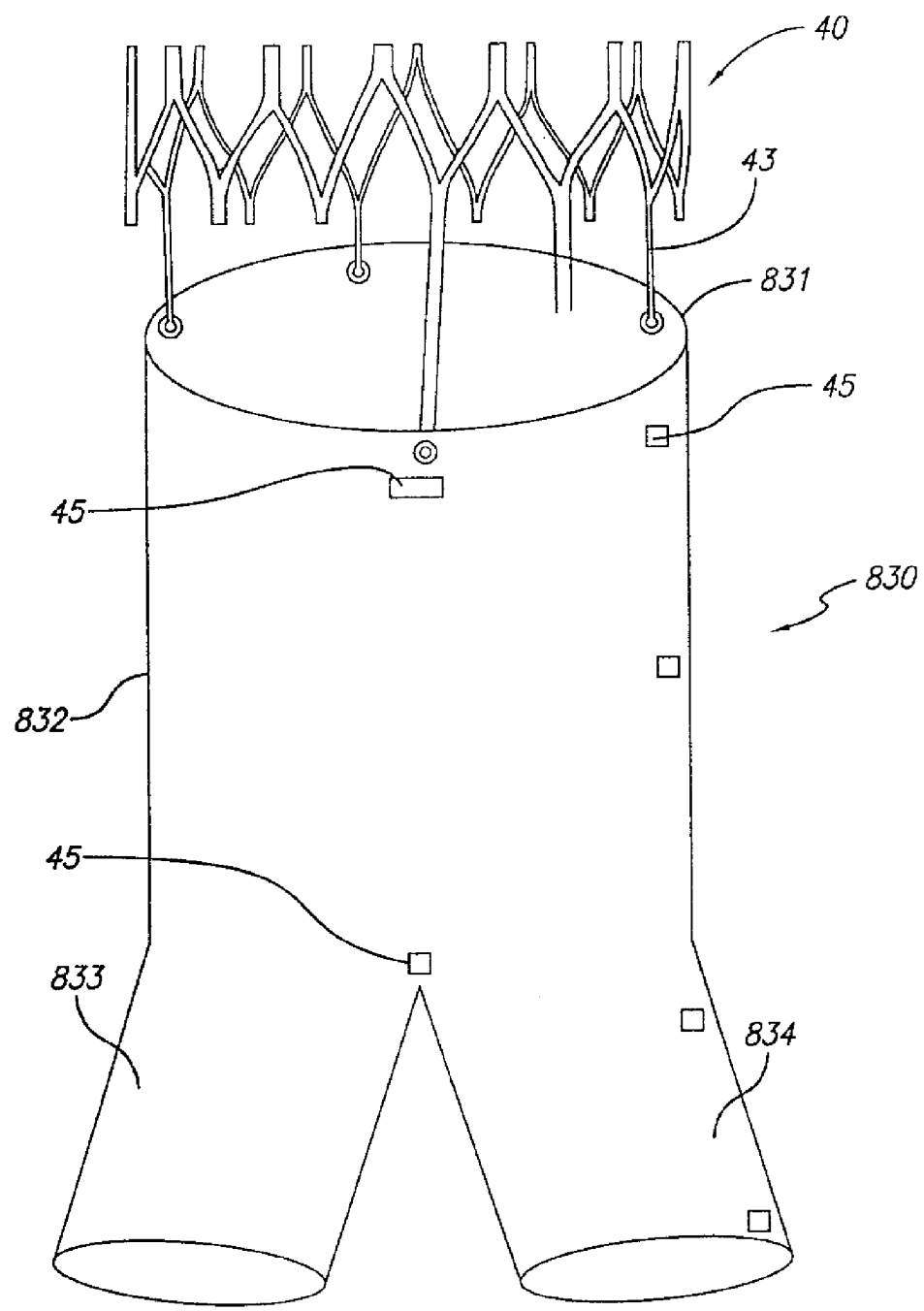
FIG. 10 is a partial perspective view of an embodiment of a bifurcated endovascular graft main body component with the attachment stent connector holes located to facilitate a pinwheel folding method.

To achieve the smallest diameter delivery profile, the graft implant must be compressed such that irregular folds or lumps are minimized when it is loaded into the loading capsule 112. Optimum compression of a main body component with an attachment stent already connected is achieved by folding the main graft body such that a pinwheel pattern is generated. Locating the attachment stent connector holes 35 as shown in FIG. 10 facilitates the pinwheel folding method. The connector holes are equally spaced around the circumference of the neck 831 of the main body component 830 such that two of the four connector holes are axially aligned with the bifurcation between the limb portions 833, 834.

Figure 11:
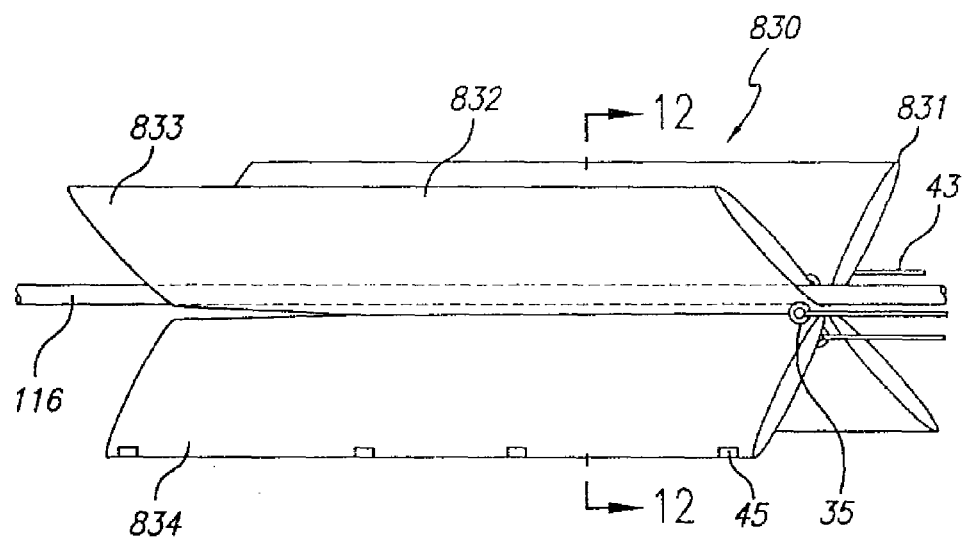
FIG. 11 is a partial perspective view of the bifurcated endovascular graft main body component depicted in FIG. 10 with the stent struts compressed and the graft material forming a smooth "cloverfold" pattern about a pusher assembly tube.

As shown in FIG. 11, a smooth "cloverfold" pattern is created when the attachment stent 40 is collapsed for delivery. The attachment stent struts 43 and connector holes 35 are pulled together, with the graft material between the attachment points pulled outward, thereby creating the "clover" or star-like pattern. With the connector holes spaced as shown, the "cloverfold" continues smoothly from the neck 831 through the limbs 833, 834.

Figure 12A:
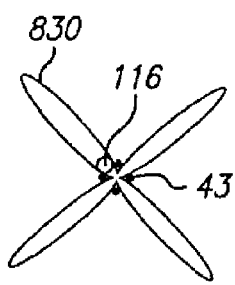
FIG. 12A is a cross-sectional view of the endovascular graft main body component depicted in FIG. 11 taken at line 12-12 before the graft is wrapped around itself.
Figure 12B:
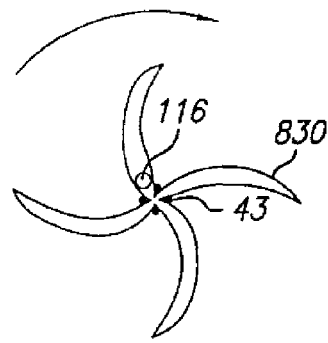
FIG. 12B is a cross-sectional view of the endovascular graft main body component depicted in FIG. 11 taken at line 12-12 as the graft is wrapped around itself.
Figure 12C:
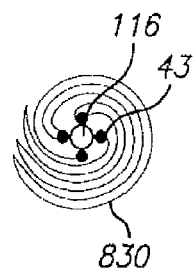
FIG. 12C is a cross-sectional view of the endovascular graft main body component depicted in FIG. 11 taken at line 12-12 with the graft compressed for delivery.

With the attachment stent collapsed and the "cloverfold" pattern heat set with an iron, the pusher assembly tube 116 is inserted through the trunk 831 and ipsi-lateral limb support portion 833. As shown in FIGS. 12A, 12B, and 12C, the "cloverfolds" are then wrapped over each other, like a pinwheel or propeller, as the graft main body component 830 is wrapped tightly around the pusher assembly inner tube 116.

Teflon tape may be used to hold the superior end of wrapped graft until it is inserted into the loading capsule 112, the tape being unwrapped as the compressed graft enters the capsule. The graft may be loaded by hand or with the aid of a tapered mandrel or mechanical loading machine. Attachment stent loading eyelets (not shown) may be provided to facilitate loading of the stent 40 and attached main body component 830.

Although the pinwheel packing method is illustrated by an attachment stent 40 with extended stent struts 43 attached to connector holes 35 in the neck 831 of the main body component 830, it is contemplated that the pinwheel packing method may be used with any of the attachment methods described herein as long as the attachment locations of the attachment stent 40 are as shown in FIG. 10. It is further contemplated that the pinwheel packing method may be applied to part or all of a graft and may be used whenever a small packing profile is desired for an endovascular graft.

The markers 45 are placed on the surface of the graft material 830 so as to form a vertical line that defines the contra-lateral side 834 of the implant 830 (see FIG. 10). The graft 830 is ironed or folded so that the markers 45 are on the valley of one of the folds. Additional markers are contemplated to be placed at the bifurcation of the graft 830 and at a superior end thereof. It is also contemplated that the markers 45 be made from 1 mm platinum coils. The marker 45 at the superior end of the graft can embody a 2.5 mm coil. When the graft 830 is on the pusher assembly inner tube 116, all the folds are wrapped around in the same direction, keeping in mind that relative twisting of the graft implant 830 between the neck 831 and limbs 833, 834 is unacceptable. For the cloverleaf fold, the markers will lie on the valley of one of the folds. As the folds are wrapped around the pusher assembly inner tube 116, the line of markers on the valley of the fold will lie next to the inner tube 116. This maintains alignment between the graft and stent during deployment. The mass of the markers in a line along side the inner tube allows for proper orientation.

Figure 12D:
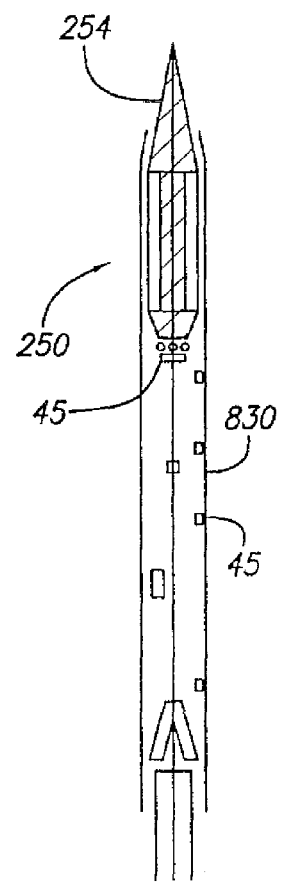
FIG. 12D is a partial cross-sectional side view, depicting a graft loaded within a delivery catheter.

Although various folding techniques are contemplated, one embodiment is to keep the markers aligned at the outer surface of the delivery system to maximize their visibility and aid in visual inspection of the packing process as well as to allow the user to verify and correct for proper orientation of the implant under fluoroscopy prior to deployment. It is contemplated that this folding technique may be used for any catheter delivered device with a graft-like component for which a specific radial orientation is desired upon deployment. Folding the main body component 830 graft implant such that the radio opaque markers 45 remain as far from the center of the delivery system as possible when packed facilitates visualization under fluoroscopy when the markers are separated far enough away from the central hypotube of the pusher, then small rotations of the delivery system tell the user which side is the contralateral side of the implant. The graft is folded and loaded into the system so that the resulting pack will have the marker bands 45 aligned along the outer surface (see FIG. 12D).

Figure 13:
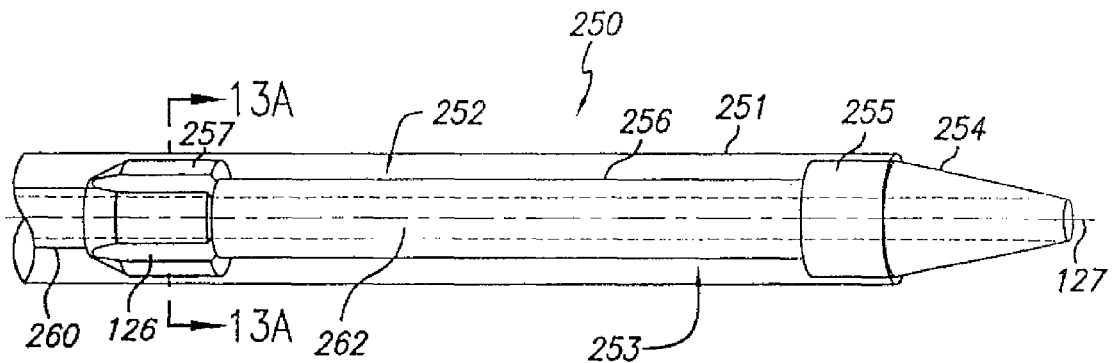
FIG. 13 is a partial perspective view, depicting an alternate delivery system of the present invention having an outer jacket covering a single piece flexible tip attached to a hypotube/lumen.
Figure 13A:
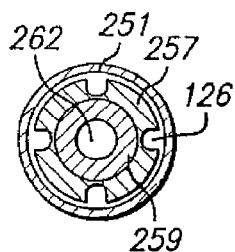
FIG. 13A is a cross-sectional view of the delivery system depicted in FIG. 13 taken at line 13A-13A.
Figure 13B:
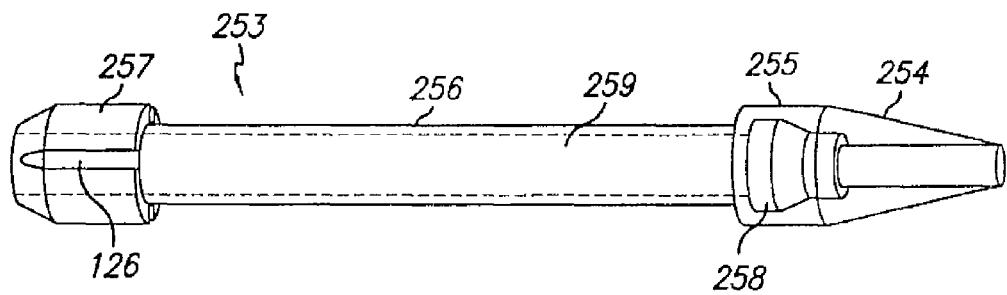
FIG. 13B is a perspective view, depicting the single piece flexible tip of the delivery system shown in FIG. 13 with the cone tip and proximal stent stop.
Figure 13C:
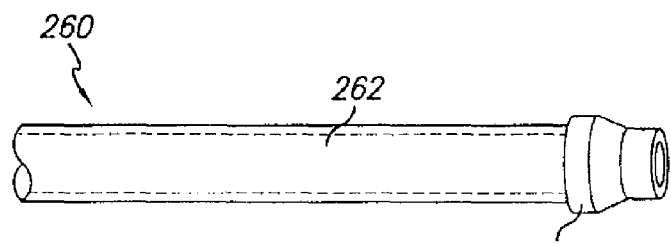
FIG. 13C is a perspective view, depicting the hypotube/lumen of the delivery system shown in FIG. 13.

FIGS. 13A-C show an alternate delivery system 250 for a self-expanding attachment stent 40 and graft implant 830. The delivery system 250 is defined by an outer jacket 251 and inner shaft 252. The inner shaft 252 is defined by a single piece flexible tip 253 mounted on a hypotube/lumen shaft 260. The flexible tip 253 is molded of a material such as Pebax, Hytrel, Silicone, or similar material and is defined by a cone tip 254, superior stent stop 255, stent inner support 256, inferior stent stop 257, internal molded mechanical stop 258, and through hole 259 therethrough which tapers near the superior end. Axial grooves 126 in the inferior stent stop 257 accommodate the extended struts 43 or other structure of an attachment stent 40. The through hole 259 of the single piece flexible tip 253 allows it to be mounted on the hypotube/lumen shaft 260. The hypotube/lumen shaft 260 is defined by a mechanical stop 261 attached to the superior end and a through hole 262 therethrough with the same diameter as the tapered end of the single piece flexible tip 253 through hole 259. The hypotube through hole 262 allows the assembled delivery system 250 to be threaded onto a guidewire 127. The single piece flexible tip 253 is attached to the hypotube 260 with glue by inserting the hypotube 260 into it and mating their respective mechanical stops 258, 261.

After the self-expanding stent 40 and graft implant 830 is compressed about the inner shaft 252 and the delivery system 250 is advanced to the treatment site, the stent 40 and implant 830 are deployed by retracting the outer jacket 251. It is contemplated that the delivery system 250 may be used to deliver and deploy any self-expanding stent 40 and graft implant 830 with a compressed diameter of 10 Fr to 25 Fr.

An alternate embodiment of the delivery system is shown in FIGS. 14-14D. The delivery system 350 has an outer jacket 251 and inner shaft 352. The inner shaft 352 is defined by a molded flexible tip 354 and a molded flexible inferior stent stop 357 mounted on a hypotube/lumen shaft 360. The flexible tip 354 is molded of a material such as Pebax, Hytrel, Silicone or similar material and is defined by a molded internal mechanical stop 258, inferior protrusion 263, and through hole 259 therethrough, the through hole 259 tapering near the superior end. The inferior end of the flexible tip 354 serves as a superior stent stop. The flexible inferior stent stop 357 is defined by axial grooves 126, a superior protrusion 264, internal mating grooves 265, and a through hole 259 therethrough. The through holes 259 of flexible tip 354 and inferior stent stop 357 allow them to be mounted on the hypotube/lumen shaft 360. The hypotube/lumen shaft 360 is defined by a mechanical stop 261 welded to the superior end, round spot welds 266, and a through hole 262 therethrough with the same diameter as the tapered end of the flexible tip 354 through hole 259. The hypotube 360 through hole 262 allows the assembled delivery system 350 to be threaded onto a guidewire 127.

The flexible tip 354 is attached to the hypotube 360 with glue by inserting the hypotube 360 through the inferior protrusion 263 and mating their respective mechanical stops 258, 261. The inferior stent stop 357 is attached to the hypotube 360 with glue by inserting the hypotube 360 through the superior protrusion 264 and mating the round spot welds 266 with the internal mating grooves 265. Heat shrink tubing (not shown) further binds the flexible tip 354 and inferior stent stop 357 to the hypotube 360.

Another alternate embodiment of the delivery system is shown in FIGS. 15-15D. The delivery system 450 has an outer jacket 251 and inner shaft 452. The inner shaft 452 is defined by a molded cone-shaped flexible tip 454, a hard superior stent stop 455, and a hard inferior stent stop 457 mounted on a hypotube/lumen shaft 460. The flexible tip 454 is defined by a molded internal mechanical stop 358 and through hole 259 therethrough, the through hole 259 tapering near the superior end. The hard superior stent stop 455 is made of hard plastic or steel and is defined by a center body 268 with the same outer diameter as the inferior end of the flexible tip 454, a superior protrusion 269, an inferior protrusion 270, and through hole 259 therethrough. The hard inferior stent stop 457 is made of hard plastic or steel and is defined by axial grooves 126, a superior protrusion 264, and a through hole 259 therethrough. The through holes 259 of flexible tip 454, hard superior stent stop 455, and hard inferior stent stop 457 allows them to be mounted on the hypotube/lumen shaft 460. The hypotube/lumen shaft 460 is defined by round spot welds 266 and a through hole 262 therethrough with the same diameter as the tapered end of the flexible tip 454 through hole 259. The hypotube 460 through hole 262 allows the assembled delivery system 450 to be threaded onto a guidewire 127.

The hard superior stent stop 455 is attached to the flexible tip 454 with glue by inserting the superior protrusion 269 into the molded internal mechanical stop 358 until the superior stent stop 455 center body 268 is flush with the inferior end of the flexible tip 454. The mated hard superior stent stop 455 and flexible tip 454 are attached to the hypotube 460 with glue by inserting the hypotube 460 through the inferior protrusion 270, center body 268, and superior protrusion 269 of the superior stent stop 455 and into the mechanical stop 259 of the flexible tip 454. The superior-most spot weld 266 of the hypotube 460 prevents the hard superior stent stop 455 from moving in the inferior direction. The hard inferior stent stop 457 is attached to the hypotube 460 with glue by sliding the hypotube 460 through the superior protrusion 264 until the inferior-most spot weld 266 on the hypotube 460 prevents further movement. Heat shrink tubing (not shown) further binds the flexible tip 454, hard superior stent stop 455, and inferior stent stop 457 to the hypotube 460.

Another alternate embodiment of the delivery system is shown in FIGS. 16A-16D. The delivery system 550 has a tapered outer jacket 551 and inner shaft 552. The inner shaft 552 is defined by a single piece flexible tip 553 having a cone tip 554 with a wider outer diameter than the inferior stent stop 557. The inferior stent stop 557 is further defined by a stent retention mechanism (illustrated as axial grooves 126) intended to retain the distal end (illustrated as extended struts 43) of a compressed attachment stent 40 having attachment hooks or barbs 86 until the outer jacket 551 is fully retracted. The outer jacket 551 is further defined by a localized increased thickness that forms a ring 271 near a tapered superior end. The tapered superior end of the outer jacket 551 promotes gradual deployment, or "flowering", of the compressed stent 40 when the jacket 551 is retracted. The ring 271 isolates the attachment hooks or barbs 86 of the partially deployed stent 40 from the walls of the patient's vasculature 160, thereby allowing the stent 40 to be relocated prior to full deployment.

As shown in FIG. 16B, the compressed stent 40 is restrained in a compressed state about the inner stent support 256 and the attached graft 30 is restrained in a compressed state about the hypotube/lumen shaft 260 by the tapered outer jacket 551. The compressed stent 40 and graft 30 are delivered to the implant site within the patients vasculature 160 by maneuvering the delivery system 550 over a guidewire 127.

As shown in FIG. 16C, when the outer jacket 551 is retracted, the compressed stent 40 begins to partially deploy, its proximal end moving radially away from the inner shaft 552. If the outer jacket 551 is not retracted past the inferior end of the inferior stent stop 557, the axial grooves 126 restrain the distal end of the stent 40, thereby preventing the stent 40 from fully deploying and allowing it to be maneuvered within the patient's vasculature 160. The ring 271 at the tapered superior end of the outer jacket 551 isolates the partially deployed hooks or barbs 86 from the walls of the patient's vasculature 160, thereby preventing damage to the vasculature 160 if the partially deployed stent 40 is moved. By further maneuvering the delivery system 550, the partially deployed stent 40 may be repositioned using fluoroscopy, thereby allowing it to be properly relocated before it is deployed.

As shown in FIG. 16D, when the outer jacket 551 is retracted past the inferior end of the inferior stent stop 557, the distal end of the stent 40 is released from the axial grooves 126 and fully deploys. Retracting the outer jacket 551 further causes the compressed graft 30 to expand radially from the hypotube/lumen shaft 260 into the patient's vasculature 160. Once the attachment stent 40 and attached graft 30 are fully deployed, the inner shaft 552 and hypotube lumen shaft 260 are retracted through the neck 31 of the deployed graft 30.

Although the stent retention mechanism is shown as axial grooves 126 in FIGS. 16A-16D, it is contemplated that any method known in the art of retaining the distal end of a stent may be used with the tapered outer jacket 551 with a superior ring 271. It is also contemplated that the tapered outer jacket 551 with superior ring 271 may be used for the delivery and deployment of any device having a physically engaging mechanism with a compressed outer surface diameter of 8 Fr. and larger.

It will be apparent from the foregoing that, while particular forms of the invention have been illustrated and described, various modifications can be made without departing from the spirit and scope of the invention. Accordingly, it is not intended that the invention be limited, except as by the appended claims and larger.

What is claimed is:

1. A system for treating vasculature at a repair site, comprising: a first treatment component;
a first sheath having the first treatment component and configured to receive a subsequent treatment component after the first sheath is placed within the vasculature and the first treatment component is deployed, the first sheath having an inferior end and a length sufficient to extend to a repair site within the vasculature; and
a loading capsule configured to receive a subsequent treatment component, wherein the loading capsule includes a superior terminal end that is configured to mate with the inferior end of the first sheath.

2. The system of claim 1, further comprising a plurality of subsequent treatment components.

3. The system of claim 2, wherein the initial sheath is retracted to deploy treatment components at a repair site.

4. The system of claim 2, wherein the first sheath is configured to retain the plurality of subsequent treatment components in a compressed configuration.

5. The system of claim 1, wherein the first treatment component is self-expanding.

6. The system of claim 5, wherein the loading capsule is configured to releasably retain the first treatment component in a compressed configuration.

7. The system of claim 1, further comprising a guidewire.

8. The system of claim 1, further comprising a pusher assembly.

9. The system of claim 8, wherein the pusher assembly is configured to simultaneously engage a plurality of treatment components.

10. The system of claim 8, the pusher assembly includes an inner tube.

11. The system of claim 10, the inner tube including an inferior end, a superior end and an exit notch.

12. The system of claim 11, the inner tube further comprising a guidewire passageway between the superior end and exit notch.

13. The system of claim 8, wherein the pusher assembly is configured to advance treatment components substantially the length of the first sheath.

14. The system of claim 1, wherein the loading capsule and first sheath have approximately equal outer profiles at a mating juncture therebetween.

15. The system of claim 1, wherein the first sheath remains within vasculature during the delivery of multiple treatment components at a repair site.

16. The system of claim 1, further comprising:
a first fitting, the first fitting attached to the superior terminal end of the loading capsule; and
a second fitting, the second fitting attached to the inferior end of the first sheath;
wherein the first fitting and second fitting releasably connect to each other.

17. A system for treating vasculature at a repair site, comprising:
a first treatment component;
a first sheath having the first treatment component and configured to receive a subsequent treatment component after the first sheath is placed within the vasculature and the first treatment component is deployed, the first sheath having an inferior end and a length sufficient to extend to a repair site within the vasculature;
a loading capsule configured to receive a subsequent treatment component, wherein the loading capsule includes a superior terminal end that is configured to mate with the inferior end of the first sheath; and
a pusher assembly, the pusher assembly further comprising a tapered flexible tip.

18. A system for treating vasculature at a repair site, comprising:
a first treatment component;
a first sheath having the first treatment component and configured to receive a subsequent treatment component after the first sheath is placed within the vasculature and the first treatment component is deployed, the first sheath having an inferior end and a length sufficient to extend to a repair site within the vasculature;

a loading capsule configured to receive a subsequent treatment component, wherein the loading capsule includes a superior terminal end that is configured to mate with the inferior end of the first sheath; and a pusher assembly, the pusher assembly being adapted to accomplish cloverfolding of the first treatment component.

19. A system for treating vasculature at a repair site, comprising:

a plurality of endovascular graft components;

a pusher assembly configured to releasably receive each of the plurality of endovascular graft components;

a loading capsule assembly configured to receive the pusher assembly and including a superior terminal end; and an introducer sheath having an inferior end configured to mate with the superior terminal end of the loading capsule assembly and to facilitate the transfer of the plurality of endovascular graft components from the loading capsule assembly.

20. The system of claim 19, wherein the introducer sheath and the loading capsule have substantially the same outer profiles at a mating juncture therebetween.

21. The system of claim 19, further comprising a guidewire.

22. The system of claim 19, wherein each of the plurality of endovascular grafts are self-expanding.

23. The system of claim 19, further comprising:

a first fitting, the first fitting attached to the superior terminal end of the loading capsule; and a second fitting, the second fitting attached to the inferior end of the first sheath;

wherein the first fitting and second fitting releasably connect to each other.

24. A method for treating vasculature at a repair site using a system including an initial introducer sheath having an inferior end and configured to receive; an endovascular graft and configured to receive subsequent endovascular graft components carried by a loading capsule with a superior terminal end after placement of the introducer sheath within vasculature, the introducer sheath extending to the repair site, comprising:

gaining access to vasculature;

inserting initial introducer sheath loaded with the endovascular graft component within vasculature and positioning a superior end of the initial introducer sheath at the repair site; retracting the initial introducer sheath to deploy the endovascular graft component;

mating the superior terminal end of the loading capsule with the inferior end of the initial introducer sheath;

inserting a subsequent endovascular graft component in the inferior end of the initial introducer sheath;

advancing the subsequent endovascular graft component within the initial introducer sheath; and deploying the subsequent endovascular graft component at the repair site by retracting the initial introducer sheath.

25. A method for treating vasculature at a repair site using a system including an initial introducer sheath having an inferior end and configured to receive; an endovascular graft and configured to receive subsequent endovascular graft components carried by a loading capsule with a superior terminal end after placement of the introducer sheath within vasculature, the introducer sheath extending to the repair site, comprising:

gaining access to vasculature;

inserting initial introducer sheath loaded with the endovascular graft component within vasculature and positioning a superior end of the initial introducer sheath at the repair site; retracting the initial introducer sheath to deploy the endovascular graft component; mating the superior terminal end of the loading capsule with the inferior end of the initial introducer sheath;

inserting a subsequent endovascular graft component in the inferior end of the initial introducer sheath;

advancing the subsequent endovascular graft component within the initial introducer sheath; and deploying the subsequent endovascular graft component at the repair site by retracting the initial introducer sheath;

configuring a plurality of subsequent endovascular graft components on a pusher assembly; and advancing the pusher assembly first through a loading capsule and then into the introducer sheath.

* * * * *